(12) United States Patent
Kapitan et al.

(10) Patent No.: US 8,172,902 B2
(45) Date of Patent: May 8, 2012

(54) SPINAL INTERBODY SPACERS

(75) Inventors: John Kapitan, Rock Hill, SC (US); Gert Nijenbanning, Oldenzaal (NL); Guilhem Denoziére, Powder Springs, GA (US); Daniel Tomko, Dallas, GA (US)

(73) Assignee: SpineMedica, LLC, Marietta, GA (US)

( * ) Notice: Subject to any disclaimer, the term of this patent is extended or adjusted under 35 U.S.C. 154(b) by 229 days.

(21) Appl. No.: 12/503,937

(22) Filed: Jul. 16, 2009

(65) Prior Publication Data

US 2010/0016970 A1    Jan. 21, 2010

Related U.S. Application Data

(60) Provisional application No. 61/081,414, filed on Jul. 17, 2008.

(51) Int. Cl.
*A61F 2/44* (2006.01)
(52) U.S. Cl. .................................... 623/17.14
(58) Field of Classification Search .... 623/17.11–17.16; 606/246–250
See application file for complete search history.

(56) References Cited

U.S. PATENT DOCUMENTS

| | | | |
|---|---|---|---|
| 4,309,777 A | 1/1982 | Patil | |
| 4,932,969 A | 6/1990 | Frey et al. | |
| 5,370,697 A | 12/1994 | Baumgartner | |
| 5,425,772 A | 6/1995 | Brantigan | |
| 5,458,642 A | 10/1995 | Beer et al. | |
| 5,480,442 A | 1/1996 | Bertagnoli | |
| 5,534,028 A | 7/1996 | Bao et al. | |
| 5,674,294 A | 10/1997 | Bainville et al. | |
| 5,683,465 A | 11/1997 | Shinn et al. | |
| 5,893,889 A | 4/1999 | Harrington | |
| 6,375,682 B1 | 4/2002 | Fleischmann et al. | |
| 6,395,032 B1 | 5/2002 | Gauchet | |
| 6,402,785 B1 | 6/2002 | Zdeblick et al. | |
| 6,419,704 B1 | 7/2002 | Ferree | |

(Continued)

FOREIGN PATENT DOCUMENTS

FR    2730159    2/1995

(Continued)

OTHER PUBLICATIONS

Bagby, G.W., The evolution of intervertebral stabilization techniques across the species, 1st World Orothopaedic Veterinary Congress, Munich, Sep. 5-8, 2002, p. 38.

(Continued)

*Primary Examiner* — Eduardo C Robert
*Assistant Examiner* — Stuart S Bray
(74) *Attorney, Agent, or Firm* — Myers Bigel Sibley & Sajovec, P.A.

(57) ABSTRACT

Non-articulating semi-rigid spinal implants include upper and lower rigid endplates that define at least one aligned pair of rigid male and female members. The respective female member having an interior facing cavity and the respective male member facing toward the female cavity. At least one elastic member resides in each female member cavity. The device can include an optional housing with at least one bore for each of the at least one aligned pairs of female and male members. The housing bore is sized and configured to snugly encase each respective aligned pair of endplate male and female members while leaving an upper outer surface of the upper endplate and a lower outer surface of the lower endplate exposed.

3 Claims, 23 Drawing Sheets

U.S. PATENT DOCUMENTS

| | | |
|---|---|---|
| 6,419,706 B1 | 7/2002 | Graf |
| 6,468,310 B1 | 10/2002 | Ralph et al. |
| 6,520,996 B1 | 2/2003 | Manasas et al. |
| 6,527,804 B1 | 3/2003 | Gauchet et al. |
| 6,527,806 B2 | 3/2003 | Ralph et al. |
| 6,533,818 B1 | 3/2003 | Weber et al. |
| D473,650 S | 4/2003 | Anderson |
| 6,572,653 B1 | 6/2003 | Simonson |
| 6,579,318 B2 | 6/2003 | Varga et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,608,117 B1 | 8/2003 | Gvozdic |
| 6,610,093 B1 | 8/2003 | Pisharodi |
| 6,626,943 B2 | 9/2003 | Eberlein et al. |
| 6,645,248 B2 | 11/2003 | Casutt |
| 6,645,249 B2 | 11/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,705,813 B2 | 3/2004 | Schwab |
| 6,719,794 B2 | 4/2004 | Gerber et al. |
| 6,726,721 B2 | 4/2004 | Stoy et al. |
| 6,733,532 B1 | 5/2004 | Gauchet et al. |
| 6,749,635 B1 | 6/2004 | Bryan |
| 6,837,904 B2 | 1/2005 | Ralph et al. |
| 6,960,232 B2 | 11/2005 | Lyons et al. |
| 7,001,433 B2 | 2/2006 | Songer et al. |
| 7,052,515 B2 | 5/2006 | Simonson |
| 7,060,099 B2 | 6/2006 | Carli et al. |
| 7,066,958 B2 | 6/2006 | Ferree |
| 7,066,960 B1 | 6/2006 | Dickman |
| 7,074,240 B2 | 7/2006 | Pisharodi |
| 7,118,599 B2 | 10/2006 | Errico et al. |
| D533,277 S | 12/2006 | Blain |
| 7,156,876 B2 | 1/2007 | Moumene et al. |
| 7,166,131 B2 | 1/2007 | Studer et al. |
| 7,169,181 B2 | 1/2007 | Kuras |
| 7,195,644 B2 | 3/2007 | Diaz et al. |
| D539,934 S | 4/2007 | Blain |
| 7,204,897 B2 | 4/2007 | Stoy et al. |
| 7,208,014 B2 | 4/2007 | Ralph et al. |
| D541,940 S | 5/2007 | Blain |
| 7,223,292 B2 | 5/2007 | Messerli et al. |
| 7,235,102 B2 | 6/2007 | Ferree et al. |
| 7,235,592 B2 | 6/2007 | Muratoglu et al. |
| 7,250,060 B2 | 7/2007 | Trieu |
| 7,267,688 B2 | 9/2007 | Ferree |
| 7,270,682 B2 | 9/2007 | Frigg et al. |
| 7,291,150 B2 | 11/2007 | Graf |
| 7,291,171 B2 | 11/2007 | Ferree |
| 7,309,357 B2 | 12/2007 | Kim |
| 7,331,994 B2 | 2/2008 | Gordon |
| 7,393,361 B2 | 7/2008 | Zubok et al. |
| 7,419,505 B2 | 9/2008 | Fleischmann |
| 7,485,145 B2 | 2/2009 | Purcell |
| 7,563,284 B2 | 7/2009 | Coppes |
| 7,563,286 B2 | 7/2009 | Gerber |
| 7,842,089 B2* | 11/2010 | Aaron ........................ 623/17.16 |
| 2003/0023311 A1 | 1/2003 | Trieu |
| 2003/0045939 A1 | 3/2003 | Casutt |
| 2003/0199982 A1 | 10/2003 | Bryan |
| 2003/0208271 A1 | 11/2003 | Kuras |
| 2004/0024461 A1* | 2/2004 | Ferree ........................ 623/17.13 |
| 2004/0034421 A1 | 2/2004 | Errico |
| 2004/0034437 A1 | 2/2004 | Schmieding |
| 2004/0093082 A1 | 5/2004 | Ferree |
| 2004/0093087 A1 | 5/2004 | Ferree |
| 2004/0127991 A1 | 7/2004 | Ferree |
| 2004/0133278 A1 | 7/2004 | Marino |
| 2004/0143332 A1 | 7/2004 | Krueger |
| 2004/0220672 A1 | 11/2004 | Shadduck |
| 2004/0267369 A1 | 12/2004 | Lyons |
| 2005/0055095 A1 | 3/2005 | Errico |
| 2005/0055099 A1 | 3/2005 | Ku |
| 2005/0085909 A1 | 4/2005 | Eisermann |
| 2005/0113925 A1 | 5/2005 | Carli |
| 2005/0143821 A1 | 6/2005 | Zdeblick |
| 2005/0149189 A1 | 7/2005 | Mokhtar |
| 2005/0159818 A1 | 7/2005 | Blain |
| 2005/0178395 A1 | 8/2005 | Hunter |
| 2005/0192674 A1 | 9/2005 | Ferree |
| 2005/0203626 A1 | 9/2005 | Sears |
| 2005/0216081 A1 | 9/2005 | Taylor |
| 2005/0216084 A1 | 9/2005 | Fleischmann et al. |
| 2005/0216092 A1 | 9/2005 | Marik |
| 2005/0273169 A1 | 12/2005 | Purcell |
| 2005/0273170 A1 | 12/2005 | Navarro |
| 2005/0273178 A1 | 12/2005 | Boyan |
| 2006/0041314 A1 | 2/2006 | Millard |
| 2006/0074489 A1 | 4/2006 | Bryan |
| 2006/0089720 A1 | 4/2006 | Schneier |
| 2006/0116768 A1 | 6/2006 | Krueger |
| 2006/0142860 A1 | 6/2006 | Navarro |
| 2006/0149377 A1 | 7/2006 | Navarro |
| 2006/0155377 A1 | 7/2006 | Beaurain |
| 2006/0188487 A1 | 8/2006 | Thomas |
| 2006/0212119 A1 | 9/2006 | Varga |
| 2006/0217809 A1 | 9/2006 | Albert |
| 2006/0235531 A1 | 10/2006 | Buettner |
| 2006/0241765 A1 | 10/2006 | Burn et al. |
| 2006/0241772 A1 | 10/2006 | Buettner-Janz |
| 2006/0259143 A1 | 11/2006 | Navarro |
| 2006/0259144 A1 | 11/2006 | Trieu |
| 2006/0259146 A1* | 11/2006 | Navarro et al. ............ 623/17.14 |
| 2006/0276900 A1 | 12/2006 | Carpenter |
| 2007/0016301 A1 | 1/2007 | Martinez |
| 2007/0016302 A1 | 1/2007 | Dickman |
| 2007/0043441 A1 | 2/2007 | Pisharodi |
| 2007/0050032 A1 | 3/2007 | Gittings |
| 2007/0067036 A1 | 3/2007 | Hudgins et al. |
| 2007/0073403 A1 | 3/2007 | Lombardo |
| 2007/0088441 A1 | 4/2007 | Duggal |
| 2007/0093903 A1 | 4/2007 | Cheng |
| 2007/0098799 A1 | 5/2007 | Zhang |
| 2007/0162133 A1 | 7/2007 | Doubler |
| 2007/0168037 A1 | 7/2007 | Posnick |
| 2007/0179611 A1 | 8/2007 | DiPoto |
| 2007/0185579 A1 | 8/2007 | Naegerl |
| 2007/0198089 A1 | 8/2007 | Moskowitz |
| 2007/0213821 A1 | 9/2007 | Kwak |
| 2007/0233262 A1 | 10/2007 | Arnin |
| 2007/0239279 A1 | 10/2007 | Francis |
| 2007/0265626 A1 | 11/2007 | Seme |
| 2007/0270952 A1 | 11/2007 | Wistrom |
| 2007/0276495 A1 | 11/2007 | Aaron |
| 2008/0015698 A1 | 1/2008 | Marino |
| 2008/0033562 A1 | 2/2008 | Krishna et al. |
| 2008/0058931 A1* | 3/2008 | White et al. ............... 623/17.11 |
| 2008/0065216 A1 | 3/2008 | Hurlbert |
| 2008/0071379 A1 | 3/2008 | Rydell |
| 2008/0077242 A1 | 3/2008 | Reo |
| 2008/0077244 A1 | 3/2008 | Robinson |
| 2008/0077246 A1 | 3/2008 | Fehling |
| 2008/0195154 A1 | 8/2008 | Brown et al. |
| 2008/0228227 A1 | 9/2008 | Brown et al. |
| 2009/0157187 A1* | 6/2009 | Richelsoph ................ 623/17.16 |
| 2009/0192617 A1* | 7/2009 | Arramon et al. ........... 623/17.16 |

FOREIGN PATENT DOCUMENTS

| | | |
|---|---|---|
| FR | 2877833 | 11/2004 |
| JP | 3275055 | 12/1991 |
| JP | 3275056 | 12/1991 |
| JP | 05-277141 | 10/1993 |
| JP | 2005-329232 | 12/2005 |
| WO | WO 94/04100 A1 | 3/1994 |
| WO | WO 00/35382 A1 | 6/2000 |
| WO | WO 2004/016205 A2 | 2/2004 |
| WO | WO 2005/044151 A1 | 5/2005 |
| WO | WO 2007/007284 A2 | 1/2007 |
| WO | WO 2007/075878 A2 | 7/2007 |

OTHER PUBLICATIONS

Disc Motion Technologies, Flyer, Product example and description, www.discmotion.com, © 2008 (4 pages).

Spinal Concepts®, Coda® Posterior Interbody Fusion Device, Advertising Brochure Document No. 1599-0001-MKC Rev. B per DCR #1801, Sep. 2002, Spinal Concepts, Inc.

Spinal Concepts®, Cadence™ Vue, The Clear Choice, Advertising Brochure Document No. 1599-0015-MKC Rev. A per DCR #2304, Jul. 2003, Spinal Concepts, Inc.

Spinal Concepts®, Natural Selection™, Interbody Spacers, Advertising Brochure Document No. 1599-0016-MKC Rev. A per DCR #2306, Jul. 2003, Spinal Concepts, Inc.

Spinal Concepts®, Traxis™, Transforaminal Lumbar Spacer, Advertising Brochure, Spinal Concepts, Inc., date unknown but believed to be prior to Jul. 17, 2008.

* cited by examiner

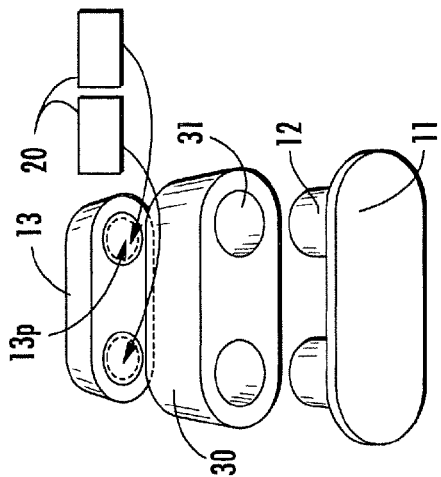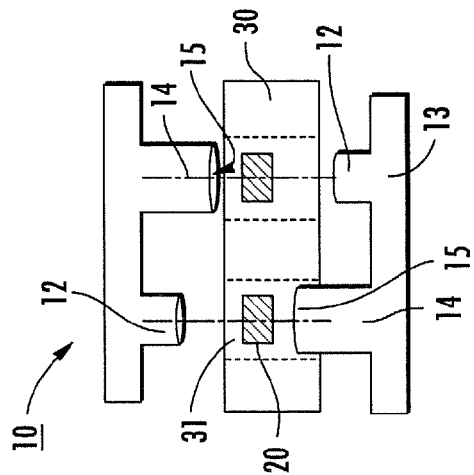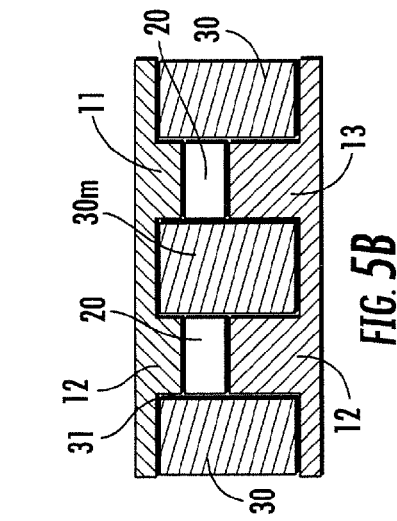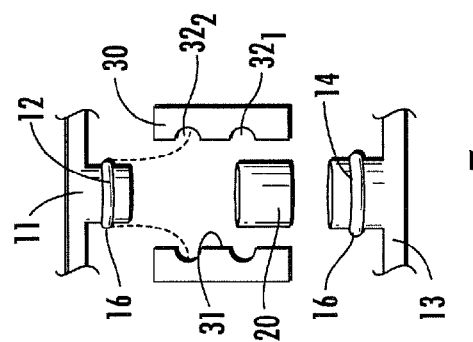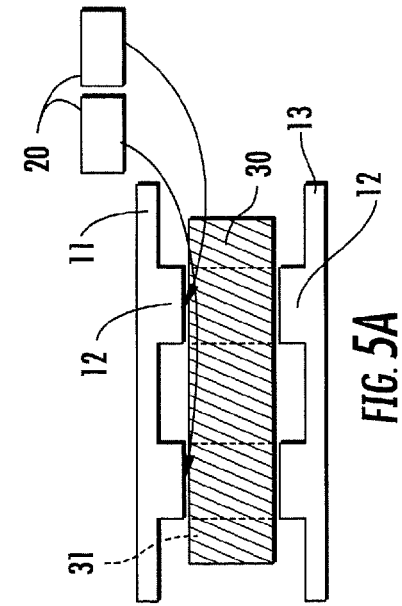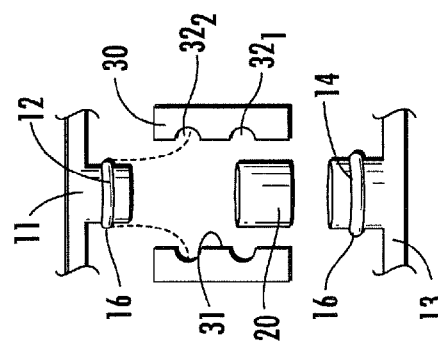

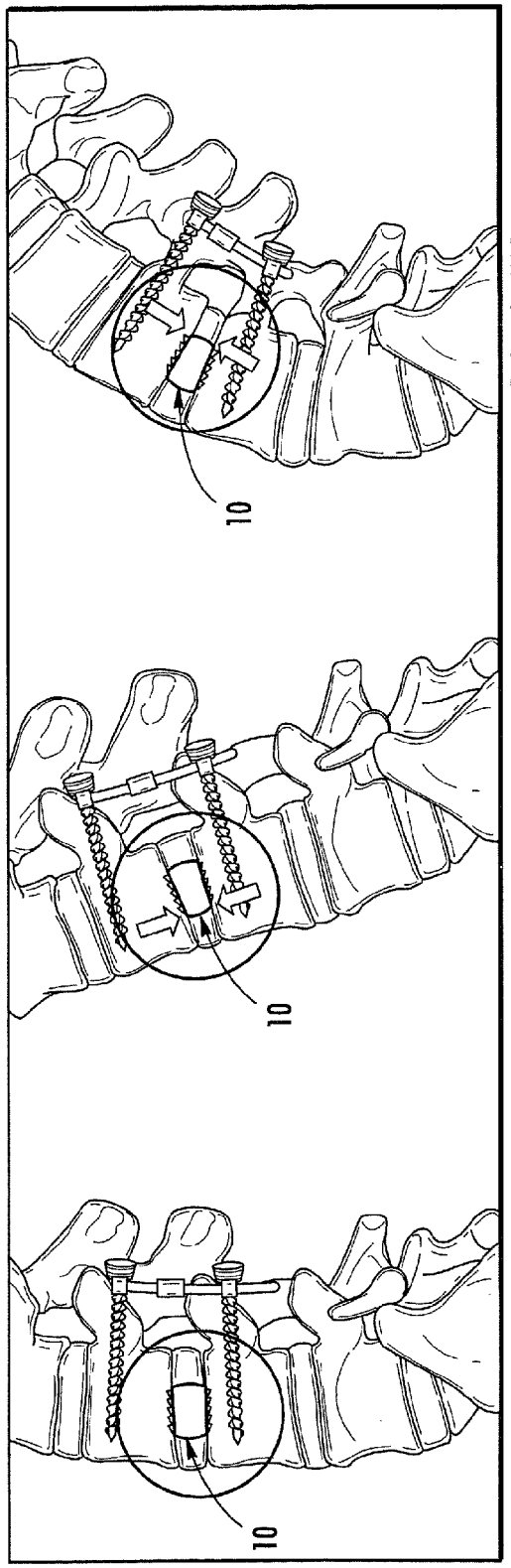

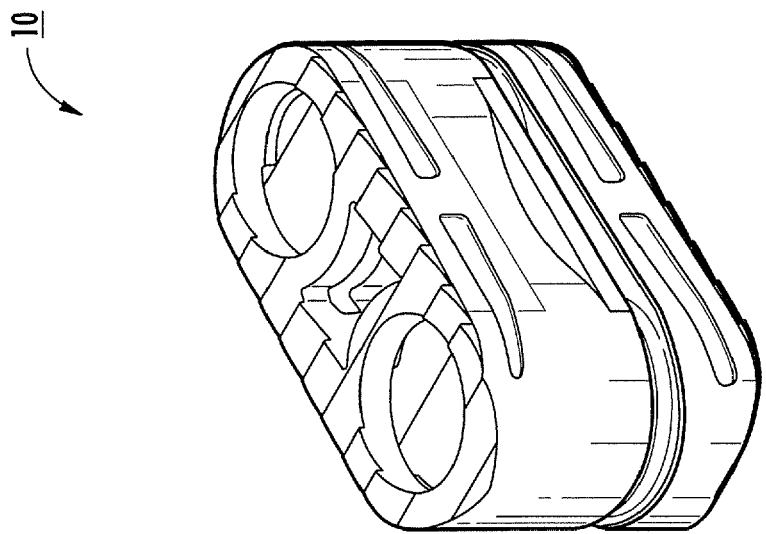
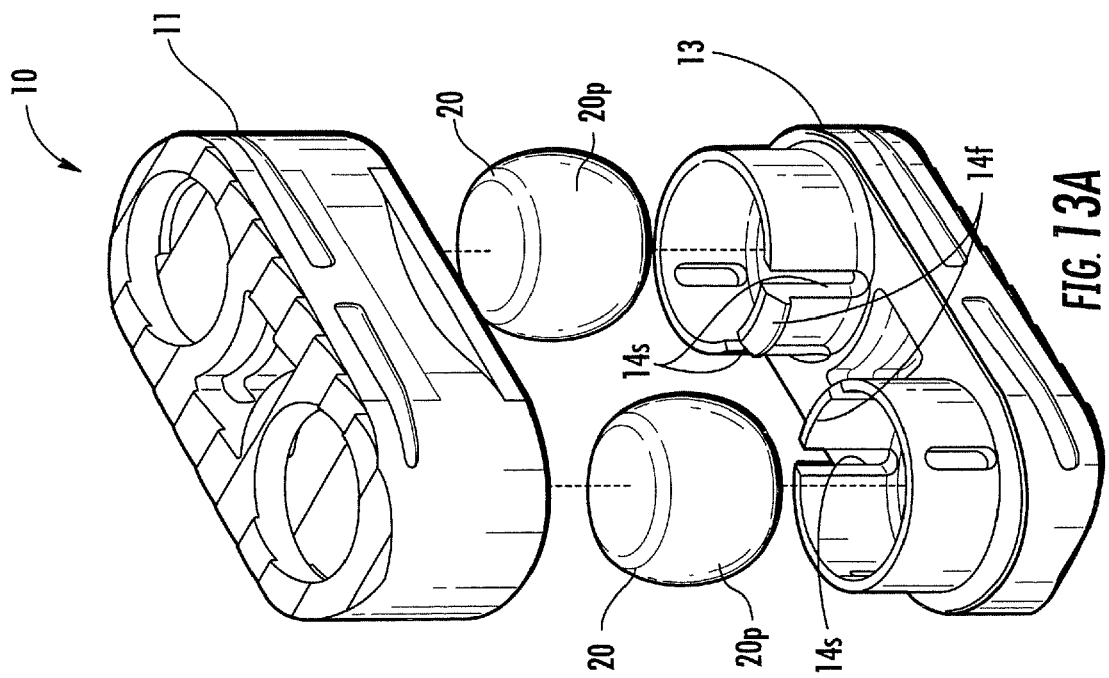
FIG. 13B
FIG. 13A

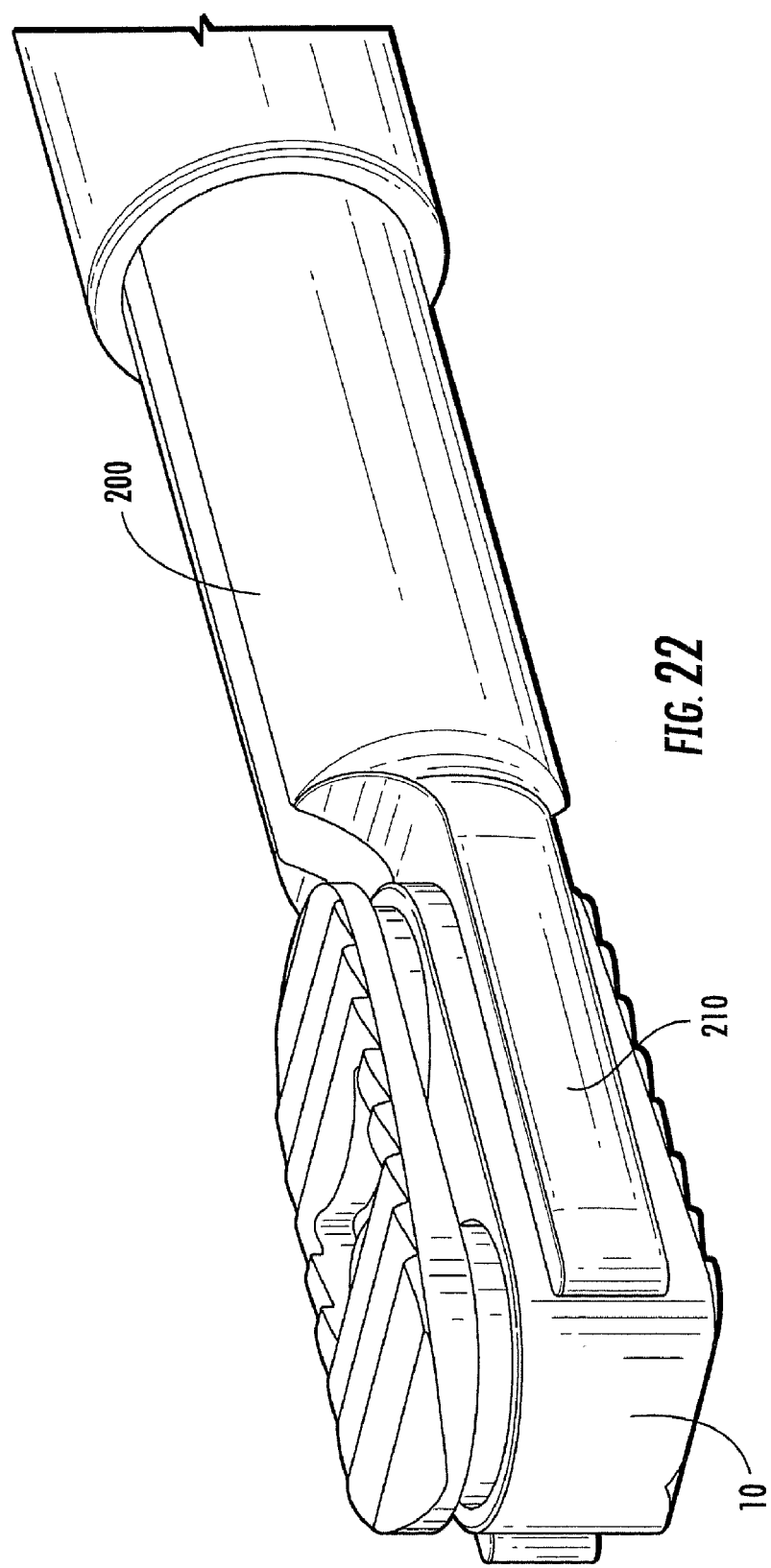

SPINAL INTERBODY SPACERS

RELATED APPLICATIONS

This patent application claims the benefit of and priority to U.S. Provisional Application Ser. No. 61/081,414, filed Jul. 17, 2008, the contents of which are hereby incorporated by reference as if recited in full herein.

FIELD OF THE INVENTION

The invention relates to spinal implants and may be particularly relevant to intervertebral body devices.

BACKGROUND OF THE INVENTION

The vertebrate spine is made of bony structures called vertebral bodies that are separated by relatively soft tissue structures called intervertebral discs. The intervertebral disc is commonly referred to as a spinal disc. The spinal disc primarily serves as a mechanical cushion between the vertebral bones, permitting controlled motions between vertebral segments of the axial skeleton. The disc acts as a joint and allows physiologic degrees of compression, flexion, extension, lateral bending, and axial rotation. The disc must have sufficient flexibility to allow these motions and have sufficient mechanical properties to resist the external forces and torsional moments caused by the vertebral bones.

The normal disc is a mixed avascular structure having two vertebral end plates ("end plates"), an annulus fibrosis ("annulus") and a nucleus pulposus ("nucleus"). Typically, about 30-50% of the cross sectional area of the disc corresponds to the nucleus. Generally described, the end plates are composed of thin cartilage overlying a thin layer of hard, cortical bone that attaches to the spongy cancellous bone of the vertebral body. The end plates act to attach adjacent vertebrae to the disc.

The annulus of the disc is a relatively tough, outer fibrous ring. For certain discs, particularly for discs at lower lumbar levels, the annulus can be about 10 to 15 millimeters in height and about 10 to 15 millimeters in thickness; cervical discs tend to be smaller.

Inside the annulus is a gel-like nucleus with high water content. The nucleus acts as a liquid to equalize pressures within the annulus, transmitting the compressive force on the disc into tensile force on the fibers of the annulus. Together, the annulus and nucleus support the spine by flexing with forces produced by the adjacent vertebral bodies during bending, lifting, etc.

The compressive load on the disc changes with posture. When the human body is supine, the compressive load on the third lumbar disc can be, for example, about 200 Newtons (N), which can rise rather dramatically (for example, to about 800 N) when an upright stance is assumed. The noted load values may vary in different medical references, typically by about +/−100 to 200 N. The compressive load may increase, yet again, for example, to about 1200 N, when the body is bent forward by only 20 degrees.

The spinal disc may be displaced or damaged due to trauma or a degenerative process. A disc herniation occurs when the annulus fibers are weakened or torn and the inner material of the nucleus becomes permanently bulged, distended, or extruded out of its normal, internal annular confines. The mass of a herniated or "slipped" nucleus tissue can compress a spinal nerve, resulting in leg pain, loss of muscle strength and control, or even paralysis. Alternatively, with discal degeneration, the nucleus loses its water binding ability and deflates with subsequent loss in disc height. Subsequently, the volume of the nucleus decreases, causing the annulus to buckle in areas where the laminated plies are loosely bonded. As these overlapping plies of the annulus buckle and separate, either circumferential or radial annular tears may occur, potentially resulting in persistent and disabling back pain.

There are several types of treatment currently being used for treating herniated or degenerated discs: conservative care, discectomy, nucleus replacement, fusion and prosthesis total disc replacement (TDR). It is believed that many patients with lower back pain will get better with conservative treatment of bed rest. For others, more aggressive treatments may be desirable.

Discectomy can provide good short-term results. However, a discectomy is typically not desirable from a long-term biomechanical point of view. Whenever the disc is herniated or removed by surgery, the disc space will narrow and may lose much of its normal stability. The disc height loss may cause osteo-arthritic changes in the facet joints and/or compression of nerve roots over time. The normal flexibility of the joint is lost, creating higher stresses in adjacent discs. At times, it may be necessary to restore normal disc height after the damaged disc has collapsed.

Fusion is a treatment by which two vertebral bodies are fixed to each other by a scaffold. The scaffold may be a rigid piece of metal, often including screws and plates, or allo- or auto-grafts. Current treatment is to maintain disc space by placement of rigid metal devices and bone chips that fuse two vertebral bodies, e.g., such as by means of a bony bridge that forms from one vertebral body to another. The devices are similar to mending plates with screws to fix one vertebral body to another one. Alternatively, hollow metal cylinders and/or carbon fiber wedge bodies can be filled with bone chips and placed in the intervertebral space to fuse the vertebral bodies together (e.g., LT-Cage™ from Sofamor-Danek or Lumbar I/F CAGE™ from DePuy). Conventional fusion devices have disadvantages to the patient in that the bones are fused into a rigid mass with limited, if any, flexible motion or shock absorption that would normally occur with a natural spinal disc.

SUMMARY OF EMBODIMENTS OF THE INVENTION

Embodiments of the invention are directed to spinal implant devices that can provide motion and/or shock absorption and may be particularly suitable as semi-rigid (or semi-flexible) interbody spacers, such as those used in fusion-type spinal therapies. However, the devices may also be suitable for non-fusion uses.

Some embodiments are directed to non-articulating spinal implants include upper and lower substantially rigid endplates that define at least one aligned pair of rigid male and female members. A respective female member has an interior facing cavity and the respective male member facing toward the female cavity. At least one (flexible) elastic member is in communication with the female and/or male members (e.g., one can optionally reside in each female member cavity, around the female cavity, on the male member or combinations of same). The device also optionally includes a housing with at least one bore for each of the at least one aligned pairs of female and male members. The housing bore may be sized and configured to encase each respective aligned pair of endplate male and female members while leaving an upper outer surface of the upper endplate and a lower outer surface of the lower endplate exposed.

Other embodiments are directed to surgical medical kits for a spinal fusion procedure for providing dynamic stabilization. The kits include a plurality of non-articulating semi-rigid interbody spacers and hardware such as at least one rod, plate and/or screw for attaching two adjacent vertebral levels together. The spacers include: (a) upper and lower rigid endplates that define at least one aligned pair of rigid male and female members, a respective female member having an interior facing cavity and the respective male member facing toward the female cavity; and (b) at least one elastic member in communication with each of the aligned female and male members.

Optionally, the spacers can also include a housing with at least one bore, one bore for each of the at least one aligned pairs of female and male members. The bore(s) is sized and configured to encase each respective aligned pair of endplate male and female members while leaving an upper outer surface of the upper endplate and a lower outer surface of the lower endplate exposed.

Still other embodiments are directed to non-articulating PLIF or TLIF interbody spinal spacers. The spacers include: (a) upper and lower rigid endplates, one having two spaced apart male members and the other having two spaced apart female members, pairs of the male and female members are longitudinally aligned, each female member having a cavity facing the respective male member; and (b) a resilient (e.g., elastically compressible) member in communication with each female and male member pairs.

The spacer endplates can have a snap-fit attachment configuration and cooperate to apply a pre-load onto the at least one elastic member held therebetween.

The spacers can optionally also include a unitary body flexible housing with two through cavities. One cavity for each of the aligned pairs of female and male members. The cavity can be sized and configured to encase each respective aligned pair of endplate male and female members while leaving an upper outer surface of the upper endplate and a lower outer surface of the lower endplate exposed.

Other embodiments are directed to methods of making non-articulating interbody spinal spacers. The methods include: (a) providing two rigid endplates, at least one having a female member with an interior facing cavity; (b) optionally attaching a first one of the rigid endplates to a flexible housing with bores extending therethrough to encase each of the at least one female members; (c) placing at least one of the elastic members (which may optionally be an elastically compressible solid plug) in each cavity; and (d) attaching the other endplate to the housing or the female member to define a non-articulating interbody spinal spacer.

The flexible housing can be a freeze-thaw molded PVA unitary body and the elastic member can also be a freeze-thaw molded solid PVA unitary body. In some embodiments the elastic member can be a plug a metal such as titanium, a polymer such as polyurethane or silicone, or stacked O-rings or washers.

The attaching step can include stretching the flexible housing over the rigid female member and engaging a retention feature on an outer surface of the female member with a corresponding channel in an inner wall of the housing cavity.

Other embodiments are directed to non-articulating semi-rigid spinal implants that include upper and lower rigid endplates that define at least two spaced apart chambers therebetween and a stack of closely spaced dome spring washers residing in each of the chambers. A plurality of the washers are oriented with the dome facing up and a plurality of the washers are oriented with the dome facing down.

Still other embodiments are directed to non-articulating semi-rigid spinal interbody spacers for fusion surgery of the spine. The spacers include upper and lower rigid endplates and at least two spaced apart unsealed chambers residing between the upper and lower endplates. The spacers also include at least one resilient member residing in each of the chambers. The implant is a non-articulating implant that provides dynamic stabilization and substantially independent compressibility responsive to loading forces applied to each chamber in the spine for each chamber. The resilient member can comprise stacked O-rings, spring washers, or a plug(s) or combinations thereof.

The upper and lower endplates can be configured to assemble together using a snap fit attachment configuration that pre-loads the resilient member.

Additional embodiments are directed to non-articulating semi-rigid spinal implants that include upper and lower rigid endplates that define at least two spaced apart annular chambers therebetween and a stack of closely spaced O-rings washers residing in each of the chambers.

Still other embodiments are directed to non-articulating semi-rigid spinal implants that include upper and lower rigid endplates that define at least two spaced apart chambers therebetween; and a single solid flexible plug residing in each of the chambers.

Further features, advantages and details of the present invention will be appreciated by those of ordinary skill in the art from a reading of the figures and the detailed description of the embodiments that follow, such description being merely illustrative of the present invention. In addition, features described with respect to in embodiment may be used in other embodiments although not specifically described therewith.

BRIEF DESCRIPTION OF THE DRAWINGS

FIG. 5A is an exploded view of an interbody spacer with a different configuration of cooperating endplates according to embodiments of the present invention.

FIG. 5B is an assembled view of the device shown in FIG. 5A.

FIG. 6A is an exploded view of an interbody spacer with yet another configuration of cooperating endplates according to embodiments of the present invention.

FIG. 6B is an assembled view of the device shown in FIG. 6A.

FIG. 7 is a schematic partial exploded view of another configuration of a housing and endplates according to embodiments of the present invention.

FIG. 8 is a schematic exploded view of yet another configuration of cooperating endplates according to embodiments of the present invention.

FIGS. 10A-10C are schematic illustrations of an interbody spacer in position and providing flexing during spinal loading according to embodiments of the present invention.

FIG. 13A is an exploded view of another interbody spacer similar to that shown in FIG. 12A according to embodiments of the present invention.

FIG. 13B is a side perspective assembled view of the device shown in FIG. 13A.

FIG. 22 is a side perspective view of a surgical instrument used to place interbody spacers according to embodiments of the present invention.

DETAILED DESCRIPTION

Figure 1:
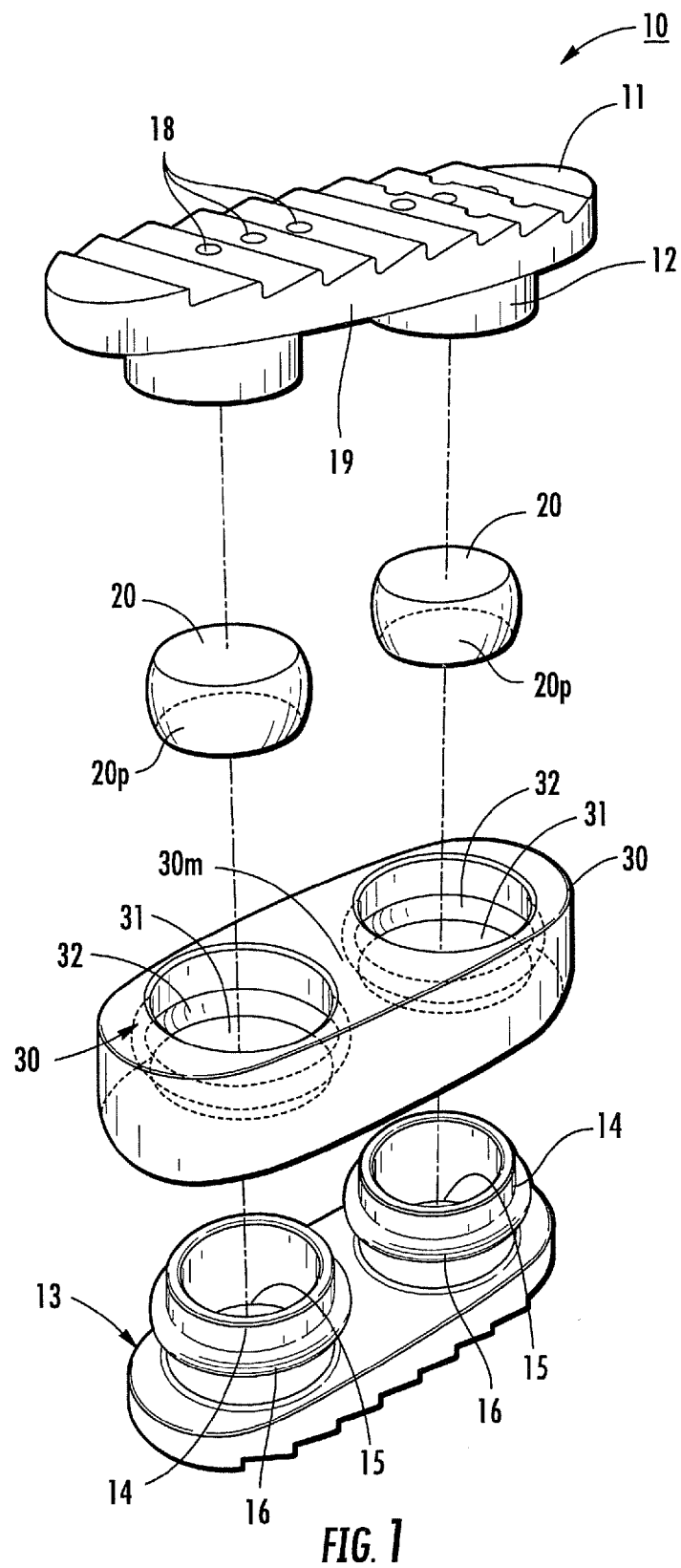
FIG. 1 is an exploded view of an exemplary interbody spacer according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The devices of embodiments of the present invention are suitable for mammalian patients, including veterinary and human subjects.

The term "semi-flexible" means that the device has the ability to at least partially resiliently deform in at least the axial direction. The term "semi-rigid" means that the device is semi-flexible and has sufficient rigidity to substantially maintain its shape under normal (non back-bending) loading in the body.

The term "barrel-like" refers to a shape that has sides that curve (taper) outwardly, then inwardly, relative to a top and/or bottom surface thereof. The term "bore" refers to a hole or passage without regard to its formation methodology. The term "piston" means that an elastic member is held snugly inside a chamber and cooperates with a compression member that can move back and forth (in a substantially axial or longitudinal direction) to exert forces on the elastic member to compress and decompress the elastic member. The terms "elastic member" and "resilient member" (or body) refers to a member that can substantially return to its original form after deformation due to normal compressive loading (in the spine).

Embodiments of the invention are particularly suitable as interbody spacers for use in spinal fusion procedures or therapies, such as, for example, posterior lumbar interbody fusion "PLIF" interbody spacers and/or as transforaminal lumbar interbody fusion "TLIF" interbody spacers. For fusion implementation appropriate fixation hardware of target vertebrae can be used with the spacer to allow for semi-flexible (dynamic) fusion implants. The term "dynamic stabilization" means that the spacer(s) and hardware allow certain types of limited motion but restrict other types of motion, such as, for example, abnormal ranges of motion. The spacers can be configured to provide compression heights of between about 1-2.5 mm, typically about 1 mm.

Generally stated, embodiments of the invention are directed to spinal implant devices that employ one or more flexible elastic members that can allow at least some motion of the spine and/or that can act as a dampening material to absorb force impacts and protect adjacent bone structures. In some embodiments, the devices can do both. The devices can be configured to allow independent compression of different regions of the device in the body.

Figure 2A:
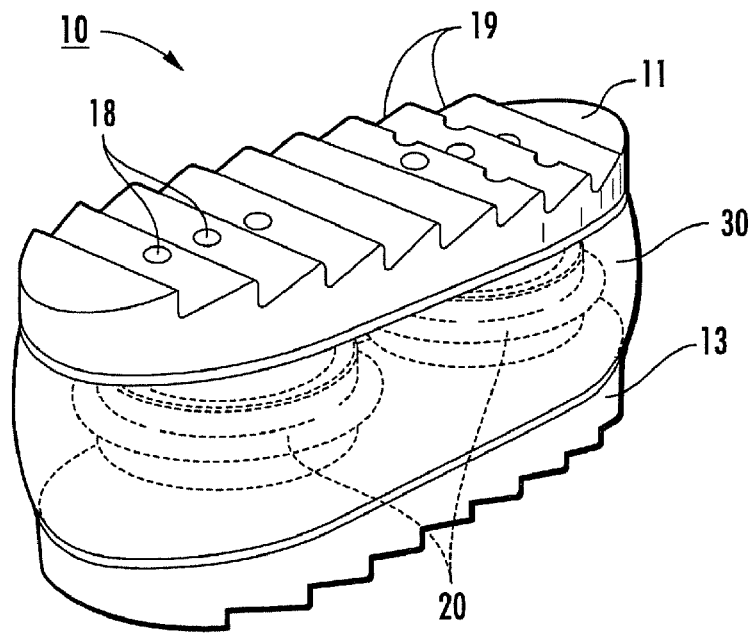
FIG. 2A is a side perspective view of the device shown in FIG. 1.
Figure 2B:
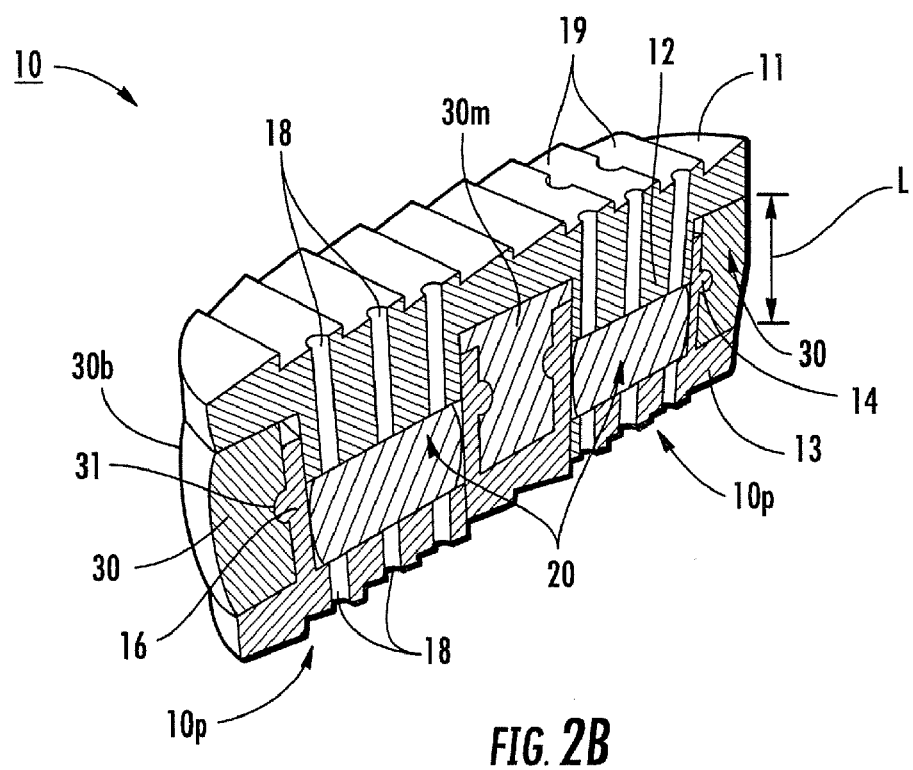
FIG. 2B is a cross-sectional view of the device shown in FIG. 2A.

FIGS. 1, 2A and 2B illustrate an exemplary embodiment of an interbody spacer 10. As shown, the spacer 10 includes upper and lower endplates 11, 13 that cooperate to be able to deform two resilient and/or elastic members 20. The elastic member 20 can be a flexible solid plug 20p as shown, but other configurations of elastic members may also be used, including metal members such as titanium bodies, O-rings, springs, washers, and the like, as will be discussed below. In some embodiments, one of the endplates (shown as the upper endplate 11) defines two spaced apart male portions or members 12 extending in an interior direction while the other endplate 13 (shown as the lower endplate) defines two corresponding female members or portions 14 with cavities 15 that are sized and configured to receive and hold the elastic members 20. The orientation of the device 10 can be inverted so that the female member cavity 15 is on the top and extends down (not shown) and the male member 12 extends up. The female member cavities 15 can have a depth dimension that is longer than the length dimension of the corresponding male member 12. The male member 12 may have an interior facing (lowermost or uppermost surface, depending on orientation) arc or dome shape or may be substantially planar or have another suitable configuration.

As shown, the spacer 10 can also include an exterior shell or housing 30 with two bores or cavities 31 that are sized and configured to snugly surround the respective female and male member pairs 12, 14 and a unitary body with a center segment 30m that spaces the two bores 31 apart. As shown in FIG. 2B, the housing body 30b can have a longitudinal dimension L and a configuration that allows the upper and lower surfaces thereof to reside proximate (typically abut) the inner faces of the upper and lower endplates 11, 13 so that there are substantially no gaps or voids between the endplate inner surfaces and the adjacent surface of the housing 30. The housing 30 typically frictionally engages both endplates 11, 13, but is not required to be sealed to upper or lower surfaces thereof. The elastic member(s) 20 can substantially fill the volume between the upper and lower surfaces of the male and female members so that there is substantially no free space therebetween irrespective of the spinal loading. Although not shown, the spacer 10 can include one or more through holes, such as formed through the endplates 11, 13 and medial portion of the housing 30m, for promoting bone ingrowth and/or fusion.

In operation, the spacer 10 may be configured so that the elastic member 20 is not affixed to either the upper or lower endplate 11, 13, and resides in a substantially non-deformed or uncompressed configuration in the female cavity 15 in communication with (typically in contact with) the male portion 12. FIG. 2B illustrates an exemplary "normal" configuration of the elastic member 20 in the spacer 10. With increased loading, the male member 12 is forced down further and deforms the elastic member 20 in the female cavity 15. The compression of the elastic member 20 is between 0.5 mm to about 3 mm, typically between about 1-2 mm, during typical bending and/or torsional loading of the spine.

In operation, the male member 12 can slide up and down relative to the female cavity 15. The configuration of the endplates 11, 13 and/or housing 30 can also prevent, inhibit or limit other motions, such as, for example, shear and axial rotation, particularly where more than one pair of male and female members 12, 14, respectively, are included.

The female members 14 can have an exterior retention or assembly locking or retention member 16 that engages the inner wall of the respective housing bore or cavity 31. The housing bore or cavity 31 can be configured to matably and/or frictionally engage the retention member 16. As shown, the retention member 16 is a circumferentially extending rib which can be continuous or semi-continuous, and the housing cavity 31 includes a channel 32 in the inner wall that matably engages the retention member 16. The retention feature of the housing 32 (where a housing is used) can be formed integrally to the inner wall (e.g., molded as a unitary body). However, other retention configurations may be used to attach the upper and lower endplates while allowing compression of the elastic member(s) 20, such as, for example, teeth, a longitudinally extending rib or ribs, teeth, and the like. In addition, the rib or ribs 16 may be formed in the housing bore inner wall and the channel 32 can be formed into the endplate female portion outer wall (not shown).

In addition, in some embodiments, as shown in FIG. 7, the male member 12 of one endplate 11 may also include a retention member 16 (such as but not limited to a rib) that also engages a different channel $32_2$ in the inner wall of the housing cavity 31 while the female portion of the other endplate 13 has a retention member 16 that engages a lower channel $32_1$. The channel $32_2$ can be formed to allow some longitudinal movement of the male member 12, e.g., relative thereto, typically between about 1-3 mm, in order for the male portion or member 12 to be able to compress the elastic member 20 under appropriate loading to provide dynamic stabilization and some flexibility of the implant in conjunction with fusion of two adjacent vertebrae levels. Thus, one channel $32_1$ can be sized and configured to more snugly engage the corresponding retention feature or member 16 than the other channel $32_2$. Alternatively, the retention member or feature 16 of the male portion 12 may alternatively have a smaller dimension than that of the female portion 14, and the channels $32_1$, $32_2$ can have the same dimensions (not shown) to allow the desired longitudinal movement.

Referring to FIGS. 1, 2A, 2B and 4A, in some embodiments, at least one endplate 11, 13, and typically both endplates, may include fluid apertures and channels 18 that allow local fluid to enter into the inner chamber and contact the elastic member 20. The channels and associated entry apertures 18 can reside over each underlying or overlying female cavity 15. Also, as shown, the upper or lower external surfaces of the endplates 11, 13 can have a series of steps or ridges 19 for contacting local vertebrae. The spacer 10 can also have bone chip receptacles in the endplates 11, 13 for in-growth fixation (not shown) as is known to those of skill in the art. The spacer 10 can include one or more substantially planar porous and/or permeable membranes (not shown) that are sized and configured to overlie or reside adjacent the top and/or bottom surfaces of the elastic member 20. The membranes may be foil membranes.

Figure 3A:
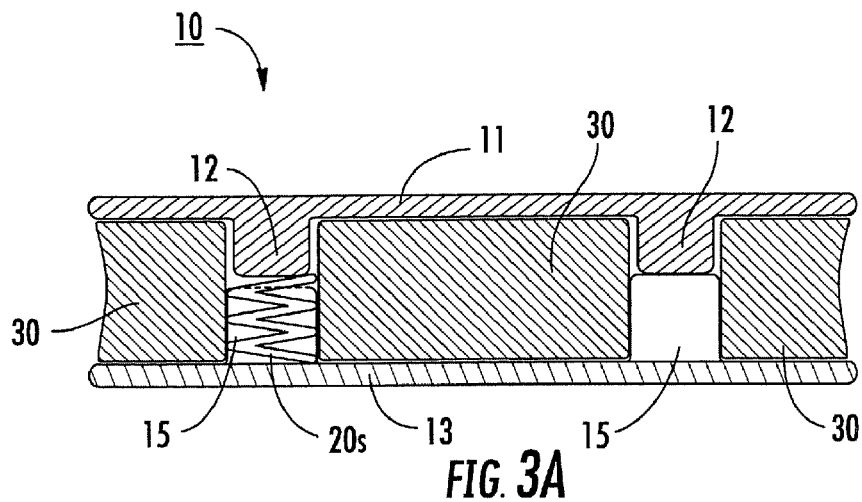
FIG. 3A is a partial sectional schematic illustration of a spacer with another flexible and elastically compressible member according to other embodiments of the present invention.

It is noted that, although shown as one elastic member 20 in each cavity 15, a plurality of (stacked) elastic or resilient members 20 may also be used to occupy or fill the desired volume. The elastic member (or elastic members) 20 can be any suitable elastic member, such as one or a plurality of flexible plugs 20p (shown in FIG. 1), or other type of elastic or resilient member. As shown in FIG. 3A, the elastic member can comprise one or more springs 20s, such as leaf springs, coil springs, Belleville springs, Clover-Dome spring washers (see, e.g., U.S. Pat. No. 6,705,813), or any other type of flexible elastic member including, for example (polyurethane or other suitable material) O-rings 20o. Combinations of different types of elastic or resilient members and/or more than one of the same type may also be used. In addition, different types of elastic members 20 can reside in different cavities of the spacer 10 (the cavity being formed by either or both the housing body cavity or female cavity 31, 15).

Figures 3B, 3C:
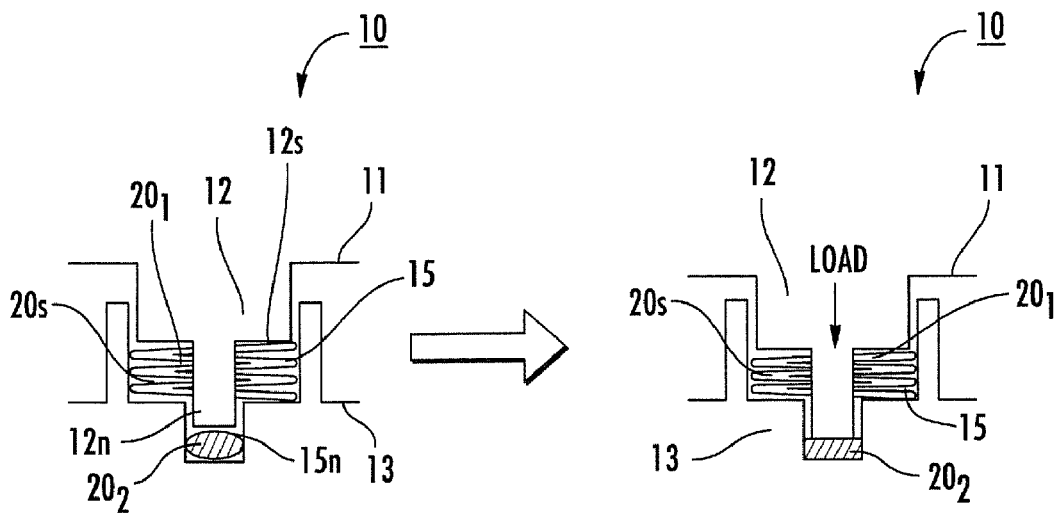
FIGS. 3B and 3C are partial sectional schematic illustrations of two flexible elastic members according to yet other embodiments of the present invention.

FIGS. 3B and 3C illustrate a configuration that uses two elastic bodies $20_1$, $20_2$ that cooperate with the endplates 11, 13. As shown, a spring 20s and small plug 20p reside between the upper and lower endplates 11, 13 and can provide shock absorption and spinal motion. The male member 12 can include a shelf 12s portion that merges into a lower neck portion 12n. The shelf portion 12s can be configured to compress a spring 20s held under the shelf and the lower endplate 13. The lower endplate 13 can include a stepped cavity configuration with a larger portion merging into a narrower lower portion 15n that is sized and configured to slidably receive the neck 12n of the male member. A flexible elastic plug $20_2$ can be held in the lower portion of the cavity 15n. The spring 20s can compress and the plug $20_2$ can deform and fill the narrow cavity 15n when substantially fully constrained. The plug 20p can provide a "soft stop" before the male and female components of the endplates bottom out. In some embodiments, maximum displacement of at least one of the endplates 11, 13 can occur when the plug 20p is deformed to fully fill the lower cavity 15n and thereby stop the downward movement of the upper endplate 11. In some embodiments, the plug $20_2$ can be substantially incompressible and may comprise or be a solid PVA hydrogel body.

Figures 3D, 3E:
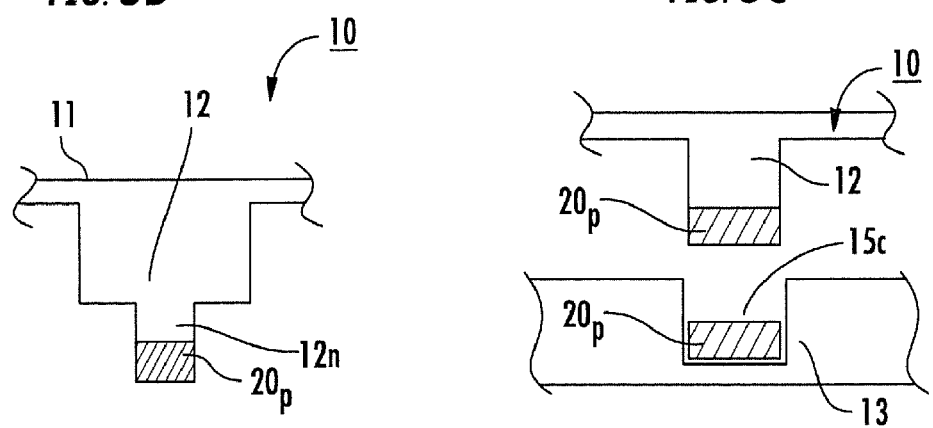
FIG. 3D is a partial sectional schematic illustration of an example of an elastic flexible body integrally attached to one of the endplates according to yet other embodiments of the present invention.
FIG. 3E is a partial sectional schematic illustration of an example of an elastic flexible body integrally attached to one of the endplates according to yet other embodiments of the present invention.

FIG. 3D illustrates that the plug 20p can be integrally attached to the male member 12. Similarly, the plug 20p shown in the embodiment of FIG. 1 can be modified as shown in FIG. 3E to be integrally attached to the male member 12. Alternatively, one plug 20p can be attached to one endplate, such as the male member, and another plug can reside in the same cavity (aligned) and under the attached plug, but not be attached. Although not shown, a plug 20p may also be attached to a floor of the female cavity 15. Where more than one plug is used, the plugs 20p (e.g., of solid polymeric material such as PVA hydrogel) can have a different durometer or stiffness rating and/or a different configuration. The plugs 20p can provide shock absorption. The elastic member can have variable stiffness, customized stiffness or multiple different stiffnesses, typically over a length direction, but optionally also side-to-side.

The plug-type elastic member 20p can be a solid unitary body of a biocompatible material, including metals and/or polymers. Some exemplary polymers include, for example, PEEK, polyurethane, silicone, hydrogels, collagens, hyalurons, polyvinyl pyrrolidone, poly HEMA, HYPAN™, Salubria®, high durometer PCU (polycarbonurethane) and other synthetic polymers that are configured to have a desired range of flexible or resilient mechanical properties, such as a suitable elastic stiffness and/or elastic modulus. The external housing 30, where used, can be formed of similar materials.

In some embodiments, the elastic member 20 is a solid molded unitary rigid polymer plug 20p such as PEEK and/or a poly-vinyl alcohol (PVA) crystalline hydrogel plug defining a semi-compressible medium. The PVA body can comprise a high molecular-weight PVA material that when solubilized (with saline or water or a suitable aqueous solution), heated, molded and subjected to several freeze-thaw cycles, produces a crystalline flexible biocompatible structure suitable for implantation in the spine. The external housing 30, where used, can again be formed of similar materials.

As noted above, in operation and position in the body, forces on the endplates 11, 13, can deform and/or compress the elastic member(s) 20. Where plugs 20p are used, the elastic member(s) 20p can have any suitable shape including spherical, box-like, cylindrical or other geometric shape, which may be hollow or solid. In some embodiments, the plug 20p can have a barrel-like shape and can have a dome or upper and/or projecting lower surface with a convex shape and fit snugly inside the female cavity 15.

In some embodiments, no housing 30 is required. In some particular embodiments, where used, the housing 30 can be formed of a biocompatible polymer. In some embodiments, the housing 30 can be a unitary polymer body that is also at least partially flexible and can have a relatively thin outer wall that covers the male/female member 12, 14 pairs. The housing 30 can be a PVA freeze-thaw solid molded flexible body that can be substantially incompressible or compressible (e.g., and can be formed of the same material as some embodiments of the elastic member(s) 20). Where both the housing 30 and the elastic member 20 are formed as solid molded freeze-thaw PVA hydrogels, the elastic member 20 may have increased rigidity or decreased rigidity relative to the housing 30.

The endplates 11, 13 (including the female and male members 14, 12 thereof) can be formed of any suitable substantially rigid biocompatible material, including, for example, ceramics, hardened polymers, and metals such as titanium or combinations thereof.

Although not shown, the elastic member(s) 20 may also include a flexible sleeve or other constraint for the elastic member(s) 20 to provide support to inhibit lateral expansion.

FIGS. 1, 2A, and 2B illustrate that in some embodiments, the spacer 10 can have a dual chamber "piston" design. The piston 10p can be defined by the endplates 11, 13 and the elastic member 20. In other embodiments, the housing bore 31 can also form a portion of the piston by defining a portion of the holding chamber such that the piston is defined by the endplates 11, 13, the housing 30 and the elastic member 20. The spacer 10 (and piston(s)) are non-articulating.

Figure 4A:
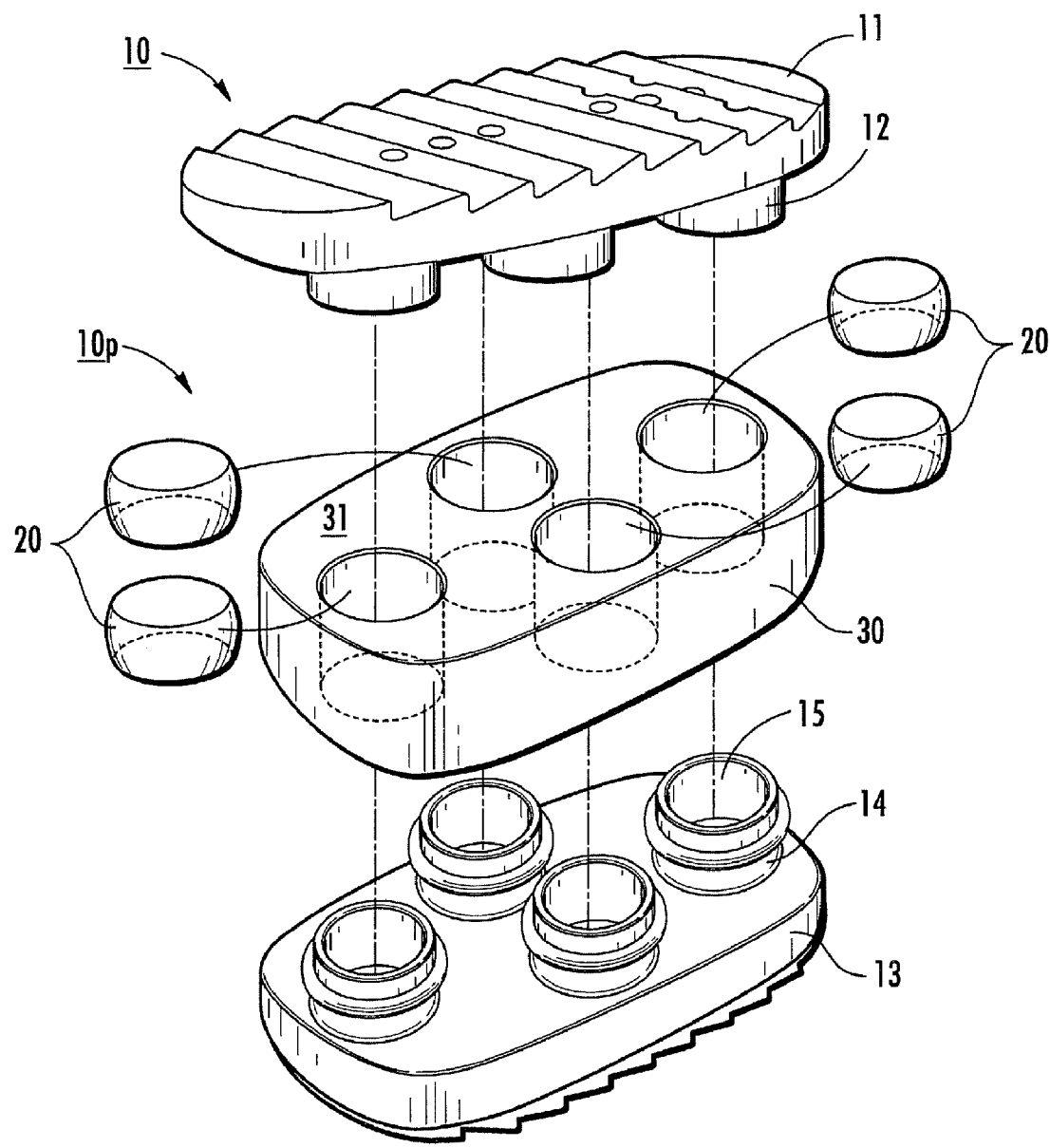
FIG. 4A is an exploded view of another embodiment of an interbody spacer having additional pistons according to embodiments of the present invention.
Figure 4B:
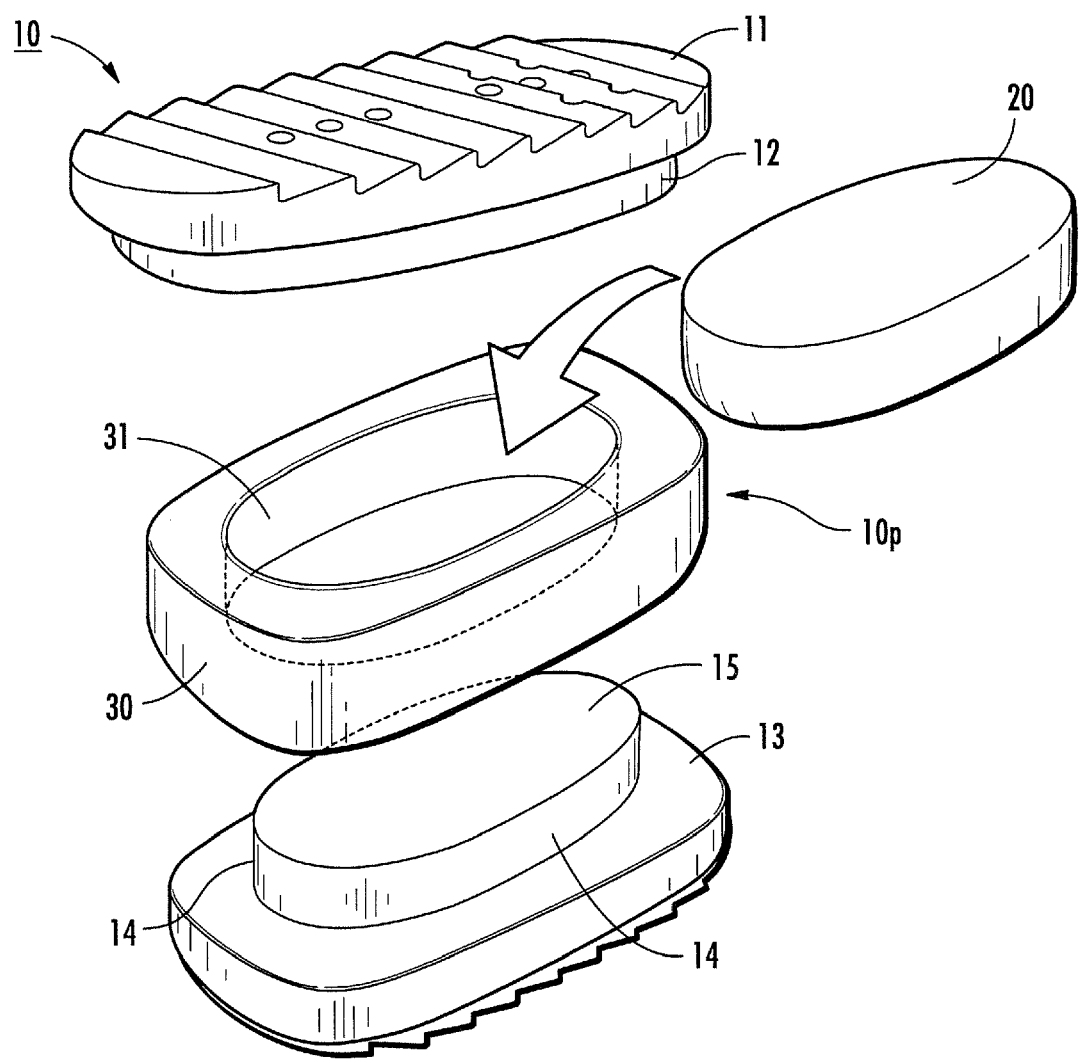
FIG. 4B is an exploded view of an interbody spacer having a single piston according to embodiments of the present invention.

It is noted that the spacer 10 can be configured with other numbers of chambers and/or pistons 10p. For example, as shown in FIG. 4A, more than two pistons 10p can be used, such as, for example, between about 3-10, shown as four. FIG. 4B illustrates that the spacer 10 can have a single piston 10p.

FIGS. 5A and 5B illustrate that each endplate 11, 13 can include a male portion or member 12 that enters into opposing end portions of the cavity 31 of the housing and can hold, block or trap the elastic member 20. In this embodiment, the housing 30 defines a portion of the sidewall of the piston chamber. One or both of the male members 12 can be configured to move in a longitudinal direction to compress the elastic member 20. The upper or lower male member 12 may have a longer length relative to the other aligned member 12.

FIGS. 6A and 6B illustrate that one of the endplates 13 shown can have a substantially planar interior facing surface 13p with the other endplate 11 having one or more male members 12. Again, the elastic member 20 is held in the cavity 31 under (or above) the male member 12. The orientation of the device shown can be reversed for implantation or positioning in the body. In this embodiment, the housing 30 defines a portion of the sidewall of the piston chamber. The planar endplate 13 may include a shallow cavity or a raised edge 13r with a groove or rib proximate each cavity 31 to engage the cavity of the housing 31. Alternatively (or additionally), the planar endplate 13 may include a ridge or groove about its perimeter to engage a receiving portion of the housing (not shown) or other housing engaging means.

FIG. 8 illustrates another embodiment of the spacer 10. In this embodiment each endplate 11, 13 may have both a female and male member 14, 12, respectively, that is aligned with the corresponding male and female member 12, 14 on the opposing side of the elastic member 20 about a housing cavity 31.

Figure 9A:
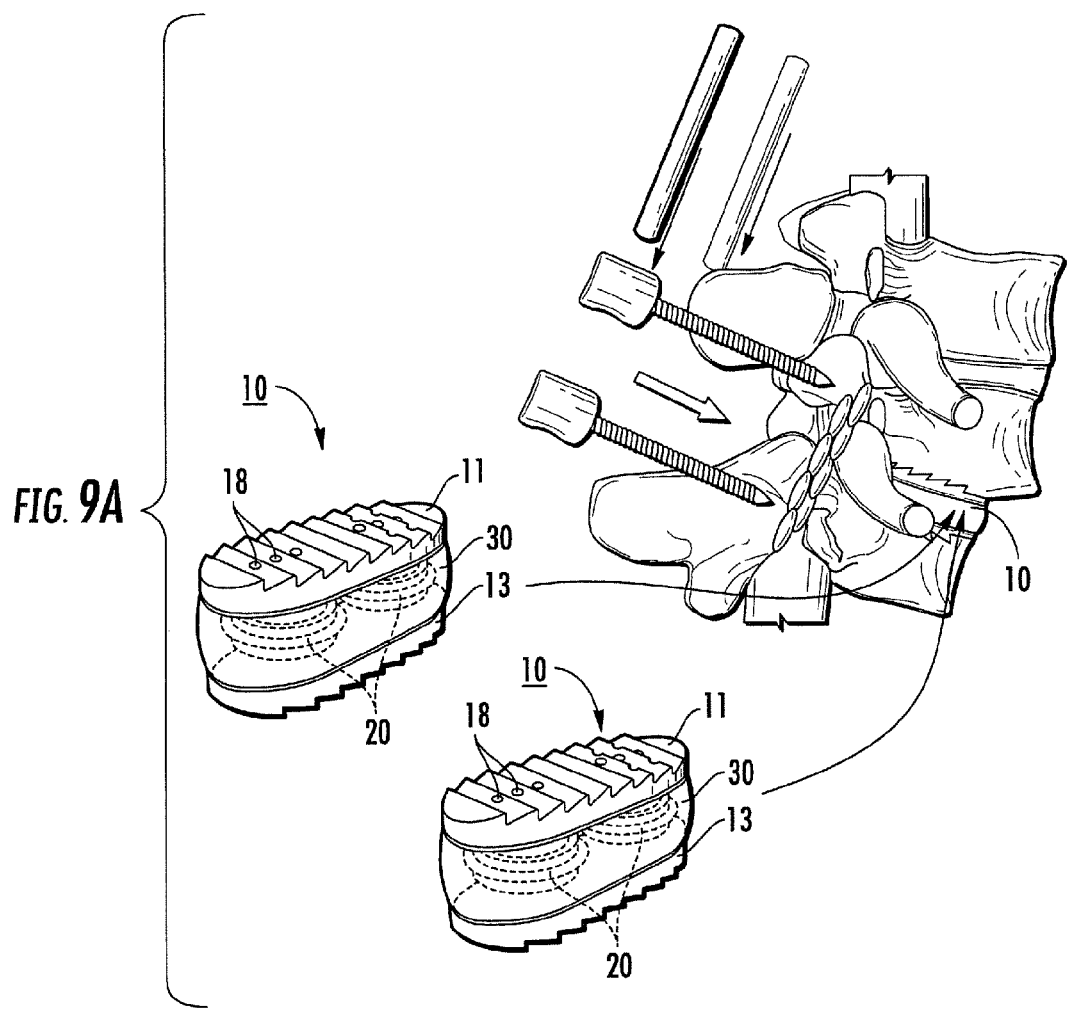
FIG. 9A is an exploded schematic view of interbody spacers used with fusion hardware according to embodiments of the present invention.
Figure 9B:
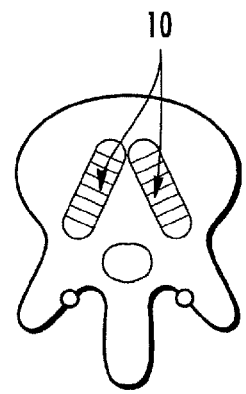
FIG. 9B is an axial view of an implant site according to embodiments of the present invention.

FIGS. 9A and 9B illustrate that two spacers 10 can be placed (side-by-side) at each vertebrae space (disc) level that is being treated and used with fusion hardware (e.g., posterior rods and screws) (the components are not shown to scale). FIGS. 10A-10C illustrates exemplary dynamic stabilization configurations of the spacers(s) 10.

Figure 11:
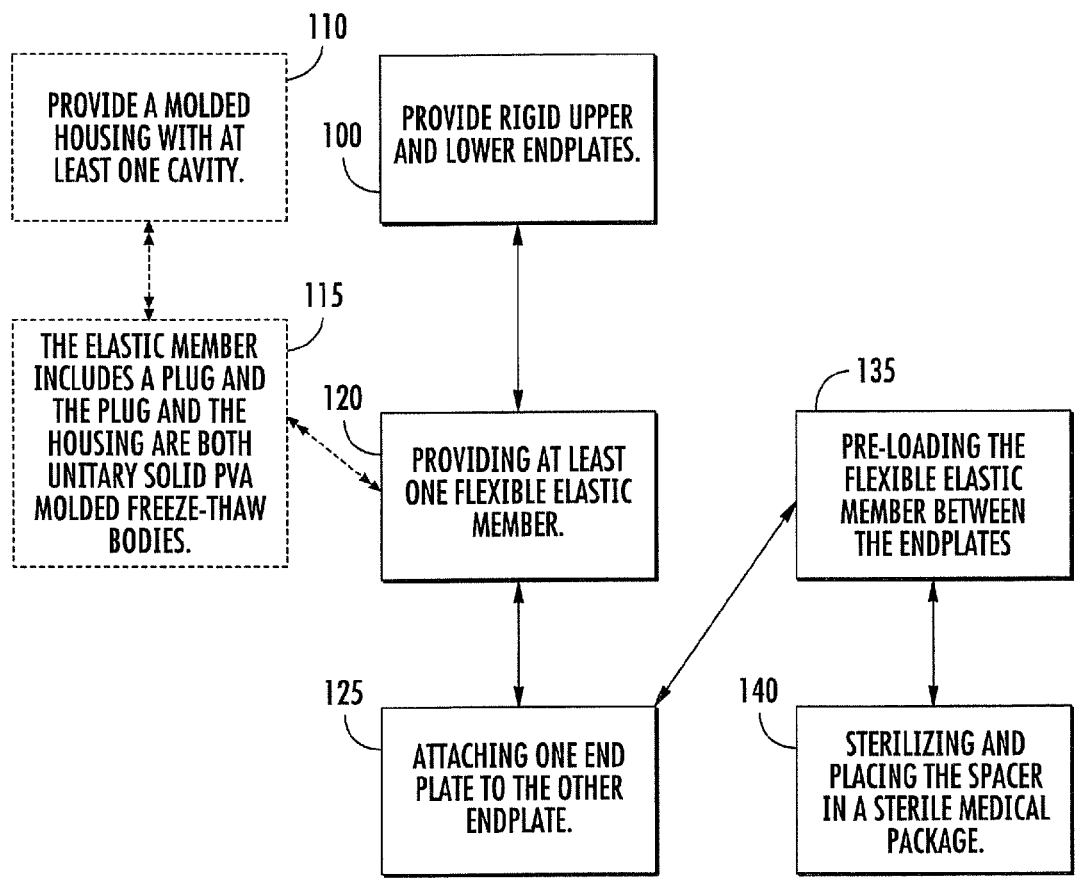
FIG. 11 is a flow chart of operations that can be used to fabricate surgical implants according to embodiments of the present invention.

FIG. 11 is a flow chart of exemplary operations that can be carried out to form a spacer according to embodiments of the present invention. Rigid upper and lower endplates are provided (block 100). At least one elastic member is provided (block 120). The elastic member and/or housing body can be unitary molded solid PVA freeze-thaw bodies (block 115). One endplate is attached to the other (block 125). The assembled endplates can be attached to preload the elastic member with a desired pre-load force/configuration (block 135) and define an interbody spinal spacer. The spacer can be sterilized and placed in a sterile medical package (block 140).

Optionally, a molded housing with at least one cavity can optionally be provided (block 110). The molded housing, where used, can be a flexible polymer and/or elastomeric primary shell. For example, the housing can be flexible and stretched to fit over and snugly encase the female members. The elastic member can be placed in the cavity or bore residing between the endplates (e.g., one or more of a plug, O'rings, springs, or washers).

Figure 12B:
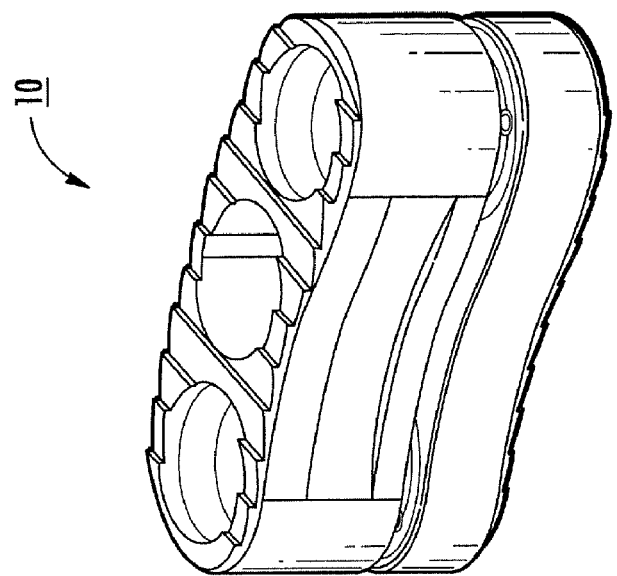
FIG. 12B is a side perspective assembled view of the spacer shown in FIG. 12A.
Figure 12A:
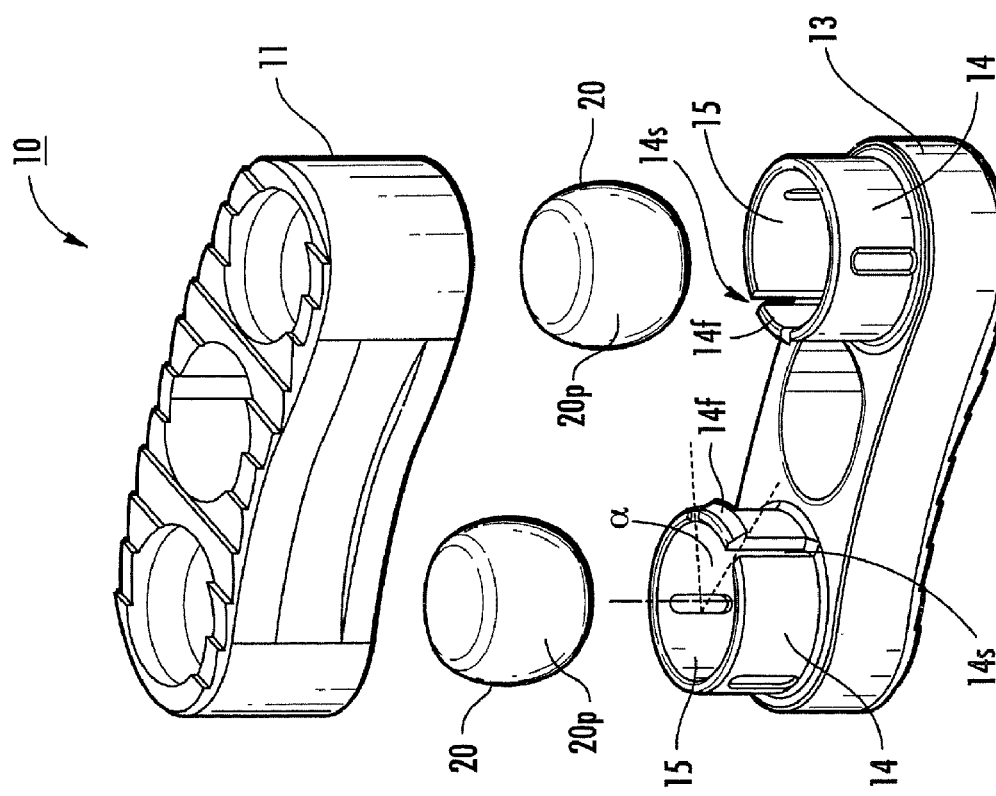
FIG. 12A is an exploded view of an interbody spacer according to embodiments of the present invention.

FIGS. 12A, 13A, 14B, 14C 15B, 17B and 18A illustrate a spacer 10 with two chambers or cavities 15. These figures also illustrate that the lower endplate 13 can include upwardly extending circular walls with inner portions having radially extending projections that form internal click fingers 14f that matably engage (e.g., snap-fit) to the upper end plate 11. In some particular embodiments, as shown for example in FIGS. 14B, 15B and 17B, the upper endplate 11 includes a wall extending downwardly with a finger 13f that matably engages an upwardly extending wall with a finger 14f of the lower endplate 13. The finger 14f may reside on an inner portion of the wall and be provided as an arc segment "α" (FIG. 12A) of between about 10-120 degrees, typically between about 15-90 degrees, and more typically between about 25-45 degrees. Upwardly extending or downwardly extending slots may reside on one or both sides of the finger 14f as shown in the figures. The recesses (particularly the two outer circular recesses) shown on the upper surface of the endplate 11 in FIG. 12A are optional and may not be used, particularly for smaller size spacers.

Figures 19A, 19B:
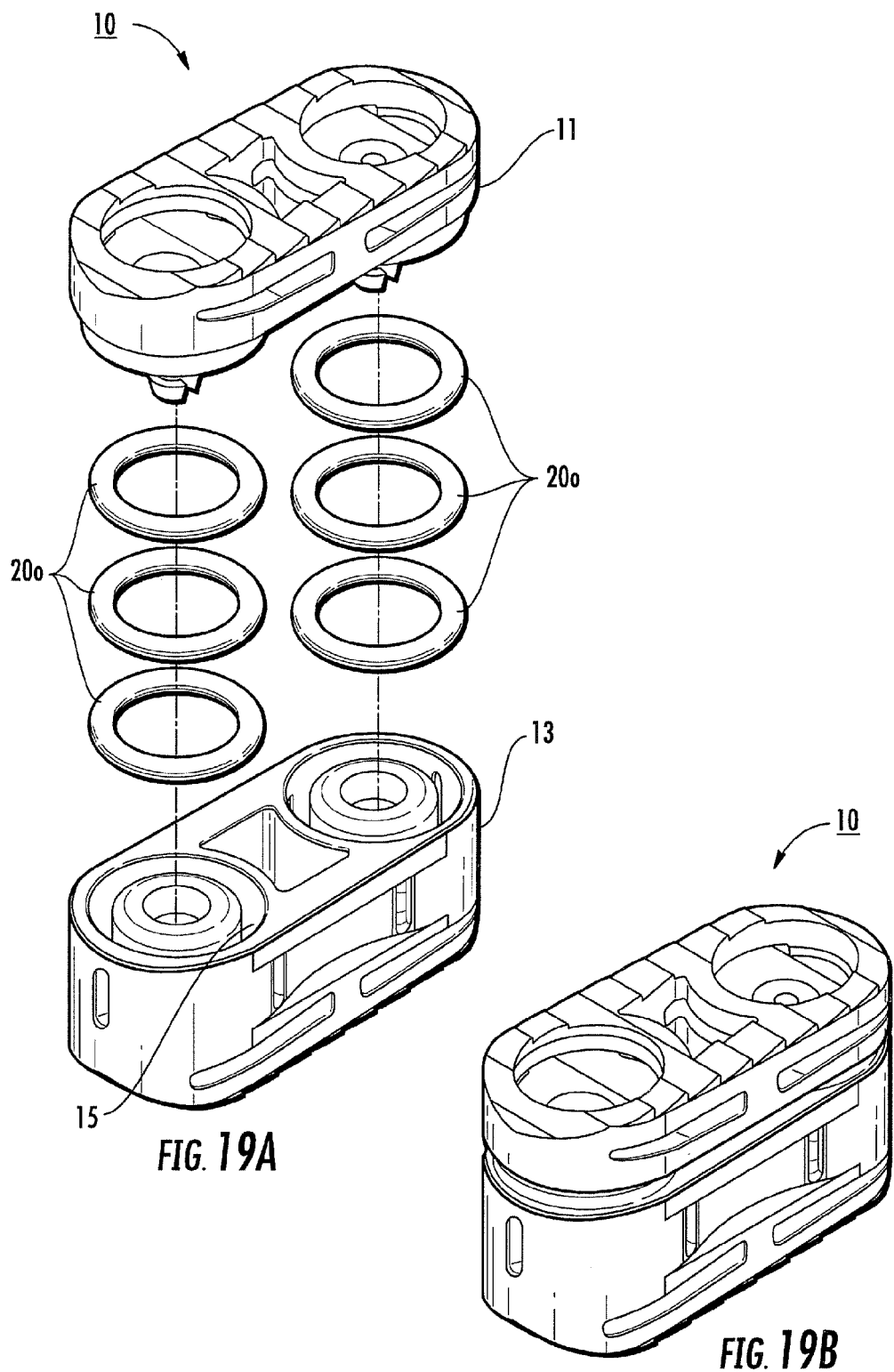
FIG. 19A is an exploded view of an interbody spacer according to embodiments of the present invention.
FIG. 19B is a side perspective assembled view of the device shown in FIG. 19A.
Figure 19C:
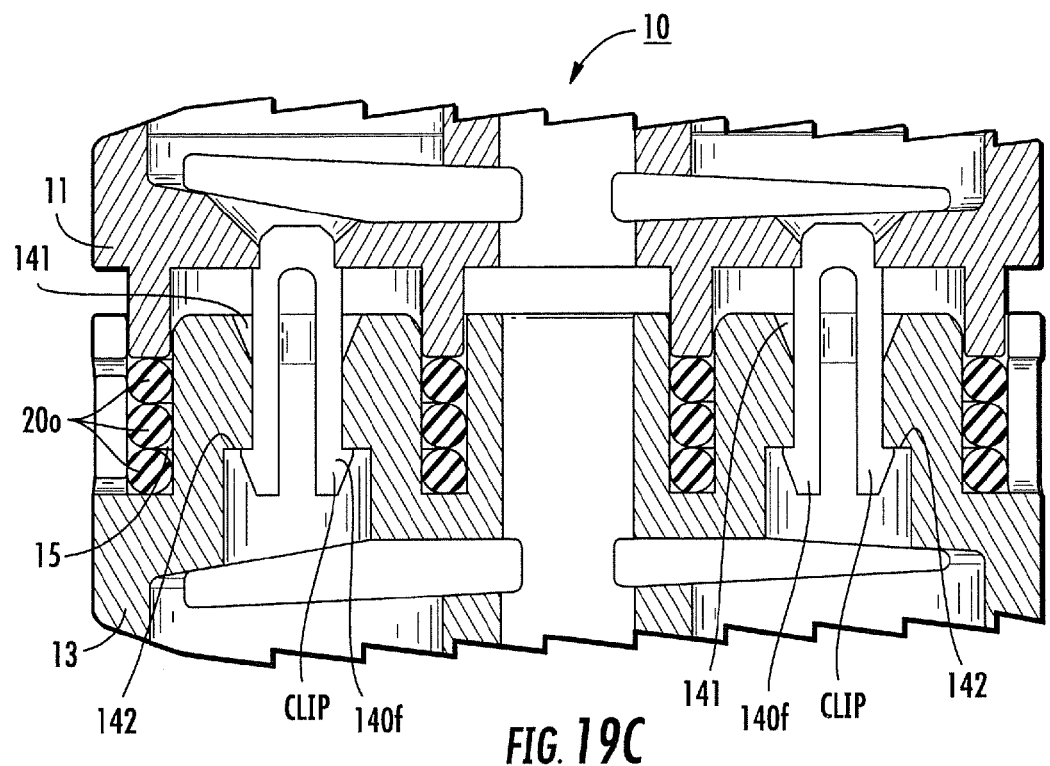
FIG. 19C is a section view of the device shown in FIG. 19A.
Figure 20A:
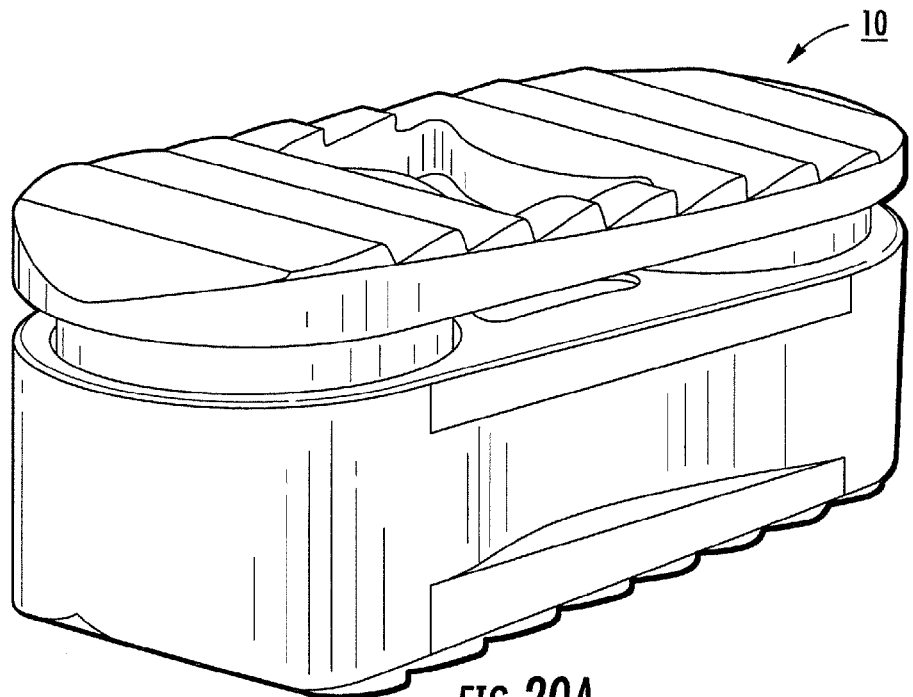
FIG. 20A is a side perspective view of yet another interbody spacer according to embodiments of the present invention.
Figure 20B:
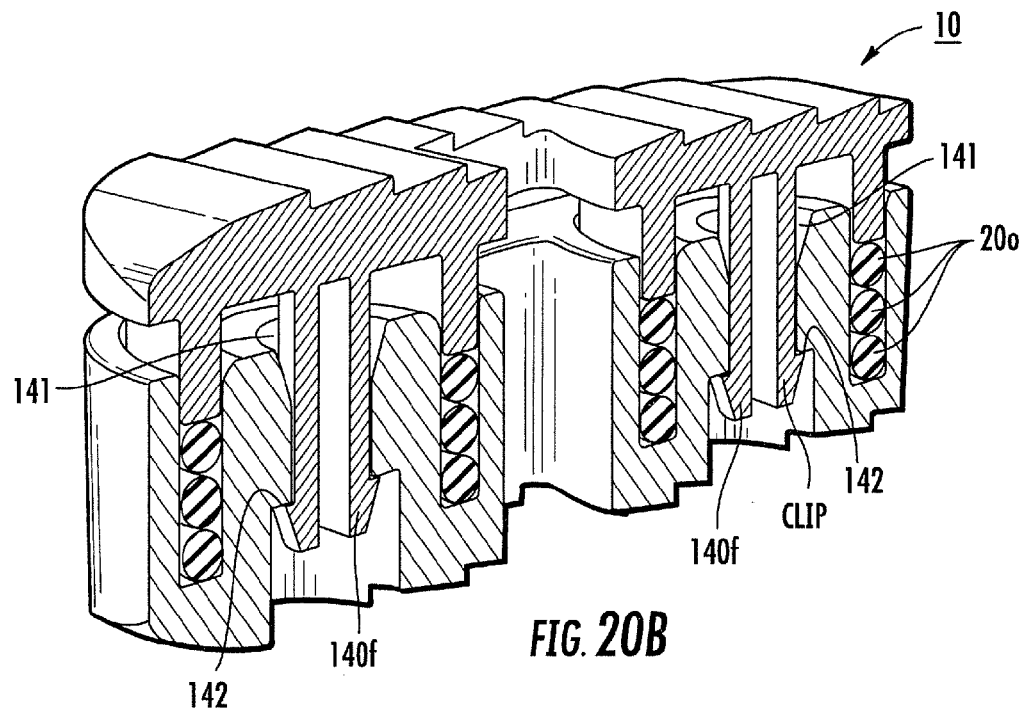
FIG. 20B is a section view of the device shown in FIG. 20A.
Figure 21A:
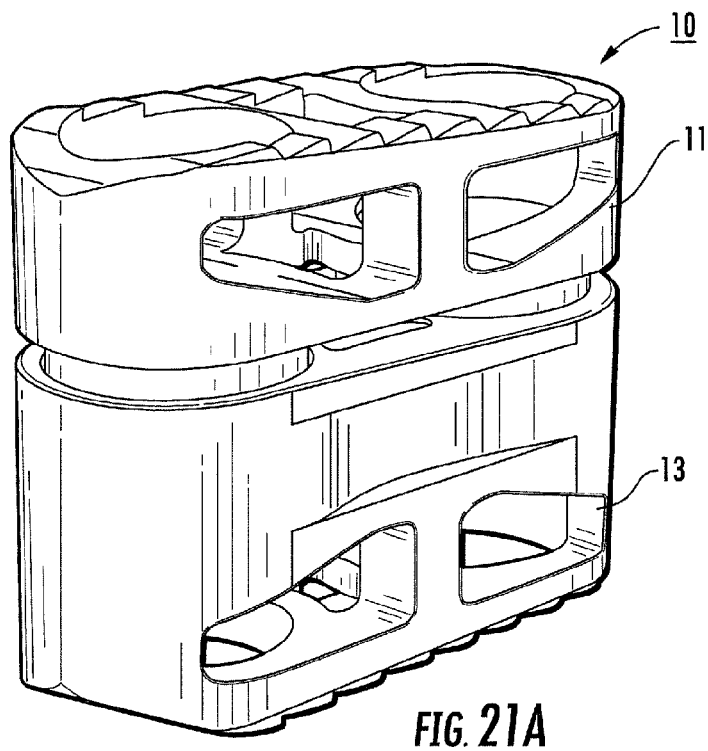
FIG. 21A is a side perspective view of another interbody spacer similar to that shown in FIG. 20A but with the O-rings held in towers or extensions according to embodiments of the present invention.
Figure 21B:
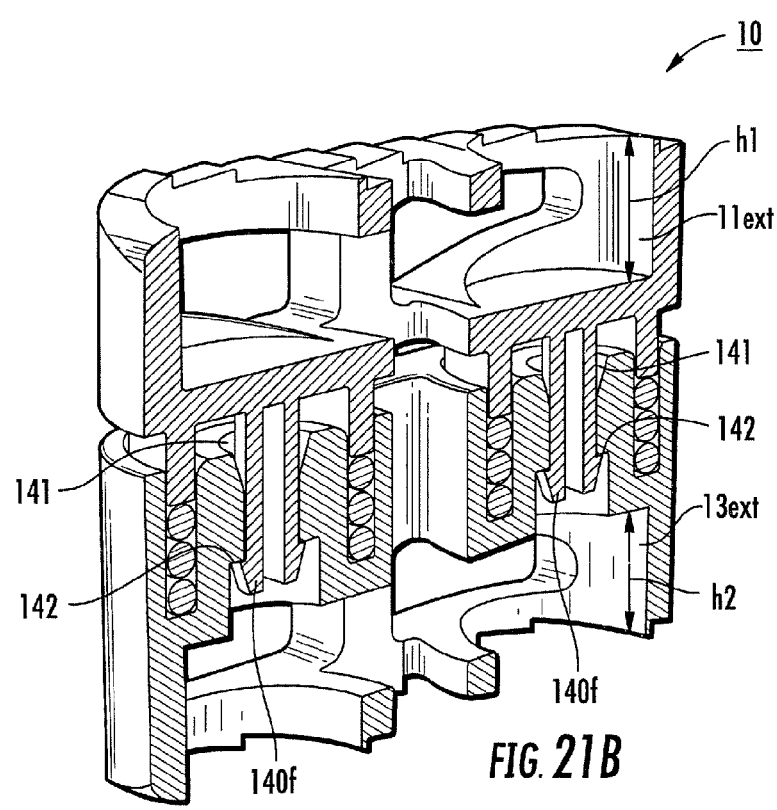
FIG. 21B is a section view of the device shown in FIG. 21A.

FIGS. 19C, 20B and 21B illustrate an alternate snap-fit or click-attachment assembly configuration. As shown, the lower end plate 13 includes an interior substantially vertically extending through-cavity. Referring to FIGS. 19C and 20B, the lower end plate 13 includes an interior (medial) substantially vertically extending through channel 141 with a lower portion having a ledge 14. The upper endplate includes a clip member 140f with a lower portion with a tapered end (finger) that abuts the female member ledge 142 to lock the upper endplate to the lower endplate. FIG. 19C illustrates that the clip member 140f may be a different material or component that resides in an aperture in the upper endplate and is used to attach the upper endplate 11 and the lower endplate 13. FIGS. 20B and 21B illustrate that the clip member 140f can be integral with the upper endplate 11.

Figure 14A:
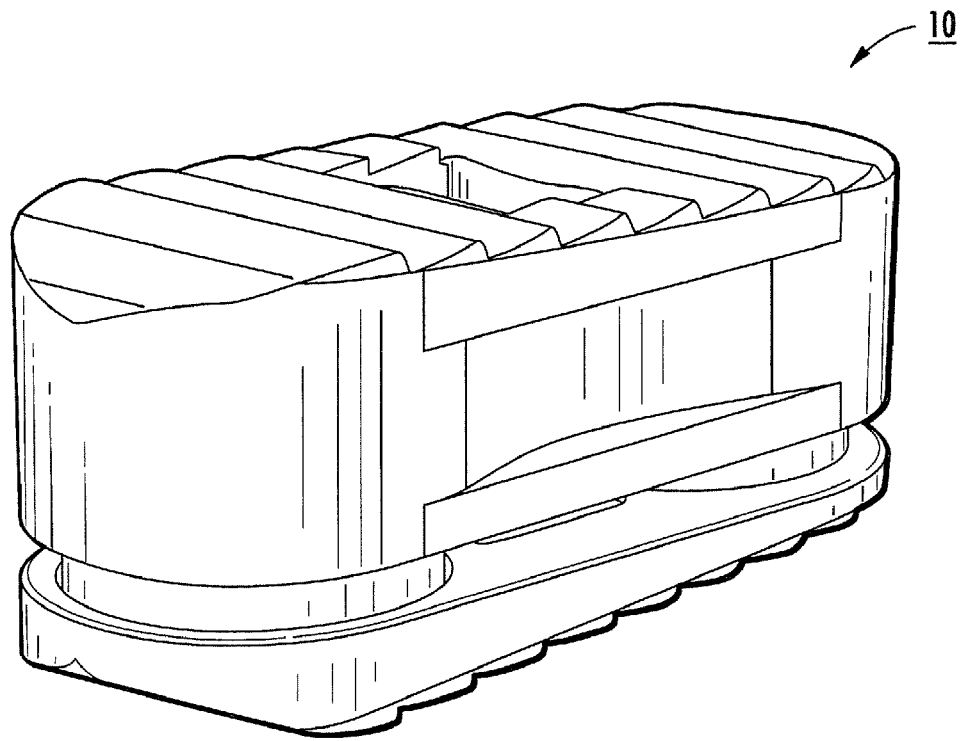
FIG. 14A is a side perspective view of an interbody spacer according to embodiments of the present invention.
Figure 14B:
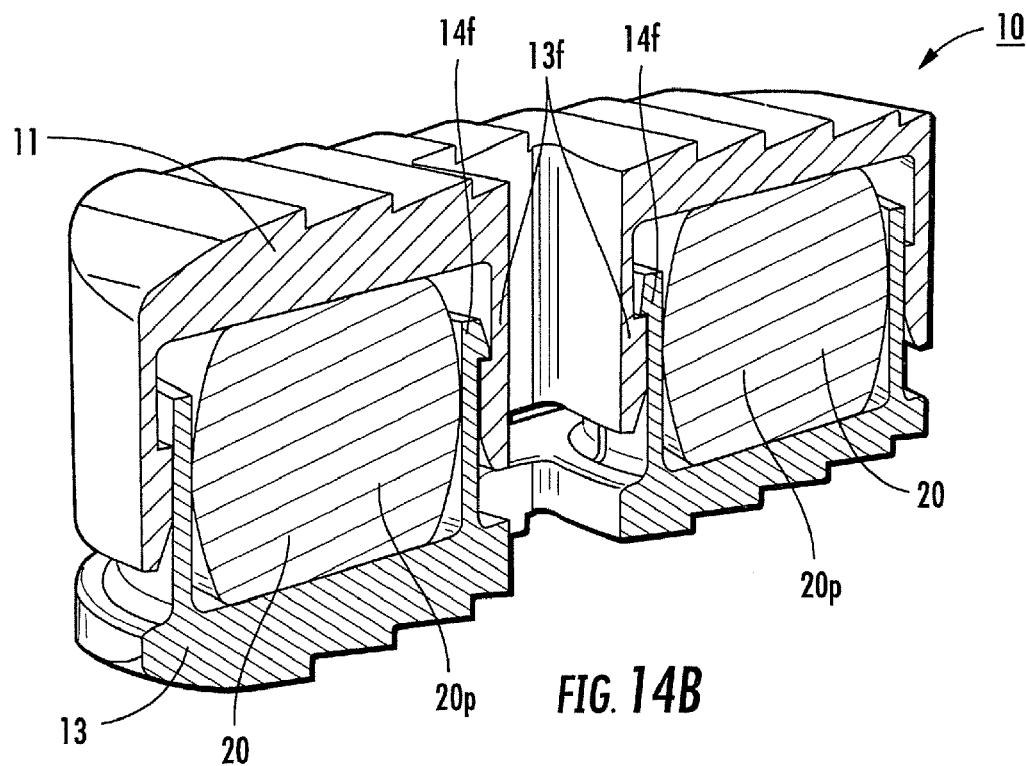
FIG. 14B is a section view of the device shown in FIG. 14A.
Figure 14C:
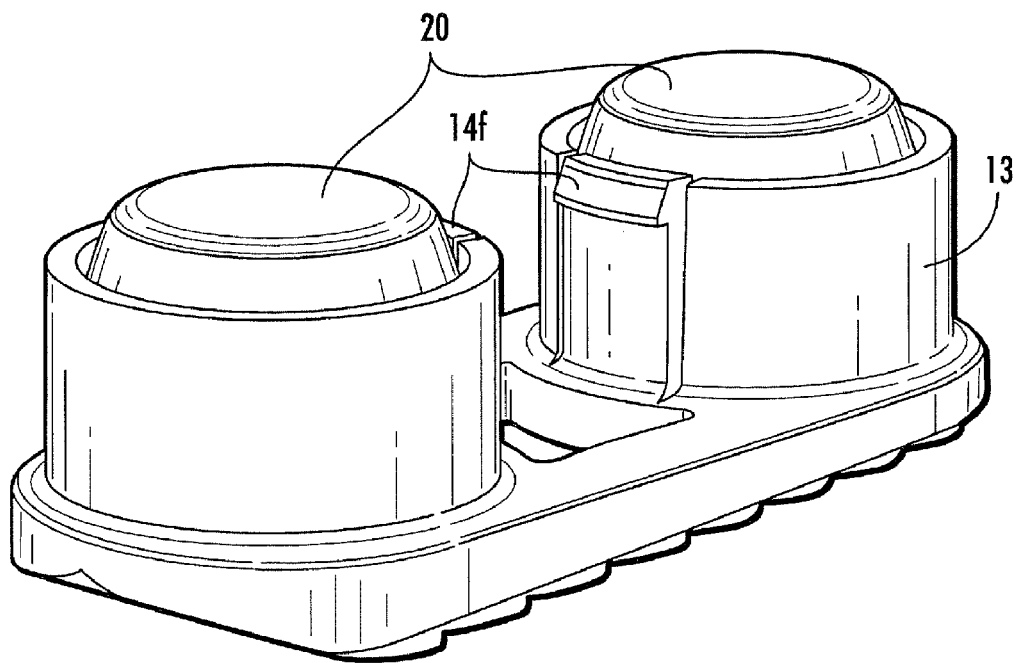
FIG. 14C is a side perspective view of the device shown in FIG. 14A without the upper endplate.
Figure 14D:
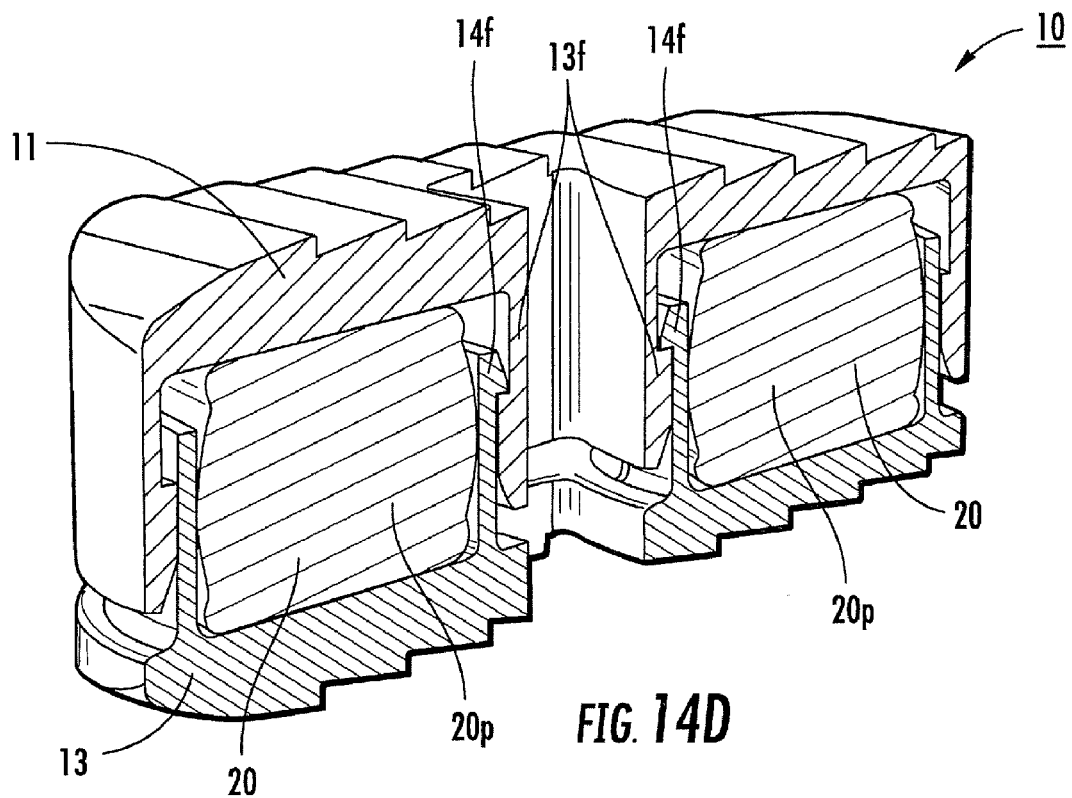
FIG. 14D is a section view of the device shown in FIG. 14B with the device having a pre-load configuration according to embodiments of the present invention.
Figure 15A:
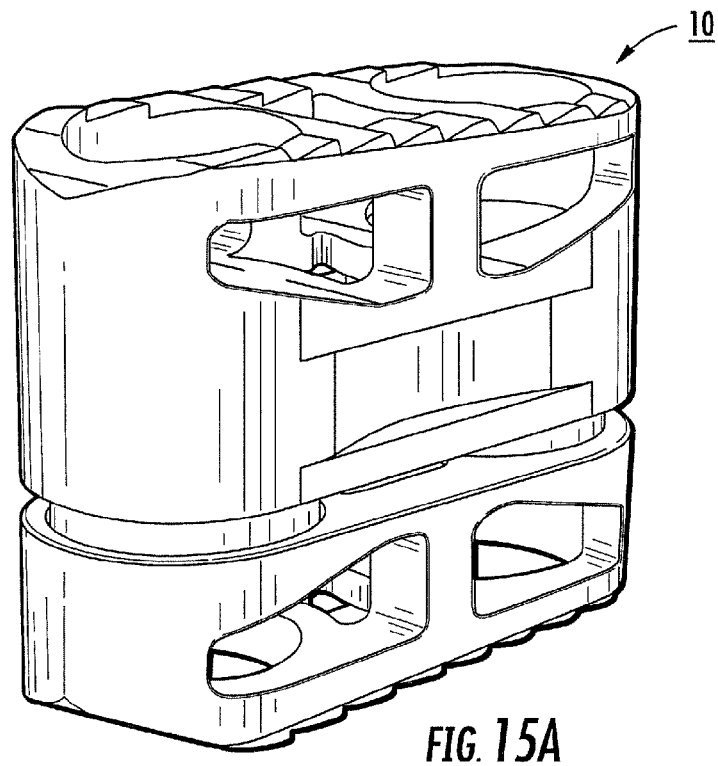
FIG. 15A is a side perspective view of an interbody spacer according to embodiments of the present invention.
Figure 15B:
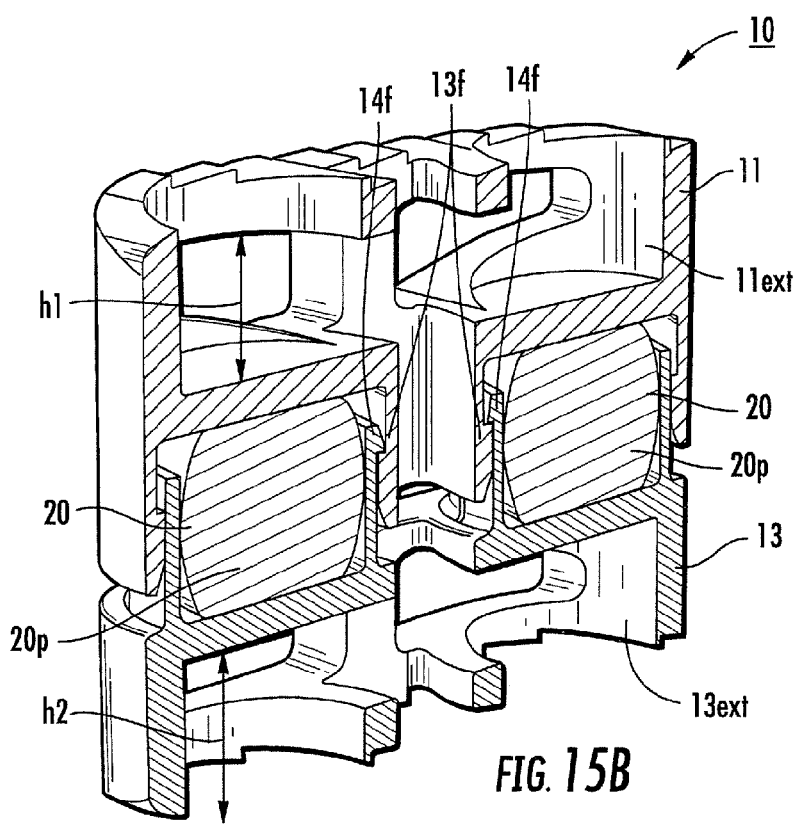
FIG. 15B is a section view of the device shown in FIG. 15A.

The upper and lower endplates 11, 13 can be configured to assemble together using the clip member 14f, 140f as a snap fit attachment configuration that pre-loads the resilient member 20 (e.g. 20p, 20o, 20s). FIG. 14D shows an example of a pre-load configuration of the spacer according to embodiments of the present invention. The pre-load can be customized to fit the particular implant location or patient requirement. Although not shown with respect to the other embodiments, the same pre-load feature can apply to other resilient members used, e.g., the O-ring 20o, or springs 20s (FIGS. 17B, 20B) when the endplates 11, 13 are snap-fitted or otherwise attached together. An exemplary range of pre-loads can be between about 10N to about 600N, typically between about 100N to 500N, but such pre-load forces may vary and be greater or lower than the forces in these ranges. The preload force can get the laxity out of the system and provide some resistance to compression in a neutral position. It is contemplated, that the pre-load can be customized or provided in different selectable ranges so that a clinician can select a pre-load based on patient-specific characteristics.

FIGS. 15A, 15B, 18A, 21A, 21B illustrate spacers with "tower" extensions 11ext, 13ext. As shown, the upper endplate 11 includes an upper portion with a surface that is configured to contact local bone and a second surface that is vertically spaced apart from and resides below the upper portion, the second surface defining a ceiling for the chamber or cavity holding the resilient member 20 (20p, 20s, 20o). The lower endplate 13 includes a lower portion with a surface that is configured to contact local bone and a second surface that is vertically spaced apart from and resides above from the lower portion. The second surface is attached to or defines the female member. The height of the gap space or extension between the upper surface and the second surface can have a height "$h_1$". Similarly, the height of the gap space or extension between the lower surface and the second surface associated with the female member can have a height "$h_2$". The heights $h_1$ and $h_2$ can be substantially the same or one may be greater than the other. In some embodiments, the $h_1$ height can be 10%-30% or more than the lower height $h_2$ or vice versa.

FIGS. 12A, 12B, 13A, 13B, 14A-14C, 15A and 15B all illustrate spacers 10 with elastic members 20 that are configured as solid or hollow plugs 20p similar to the embodiments discussed above with respect to FIGS. 1 and 2A.

Figures 16A, 16B:
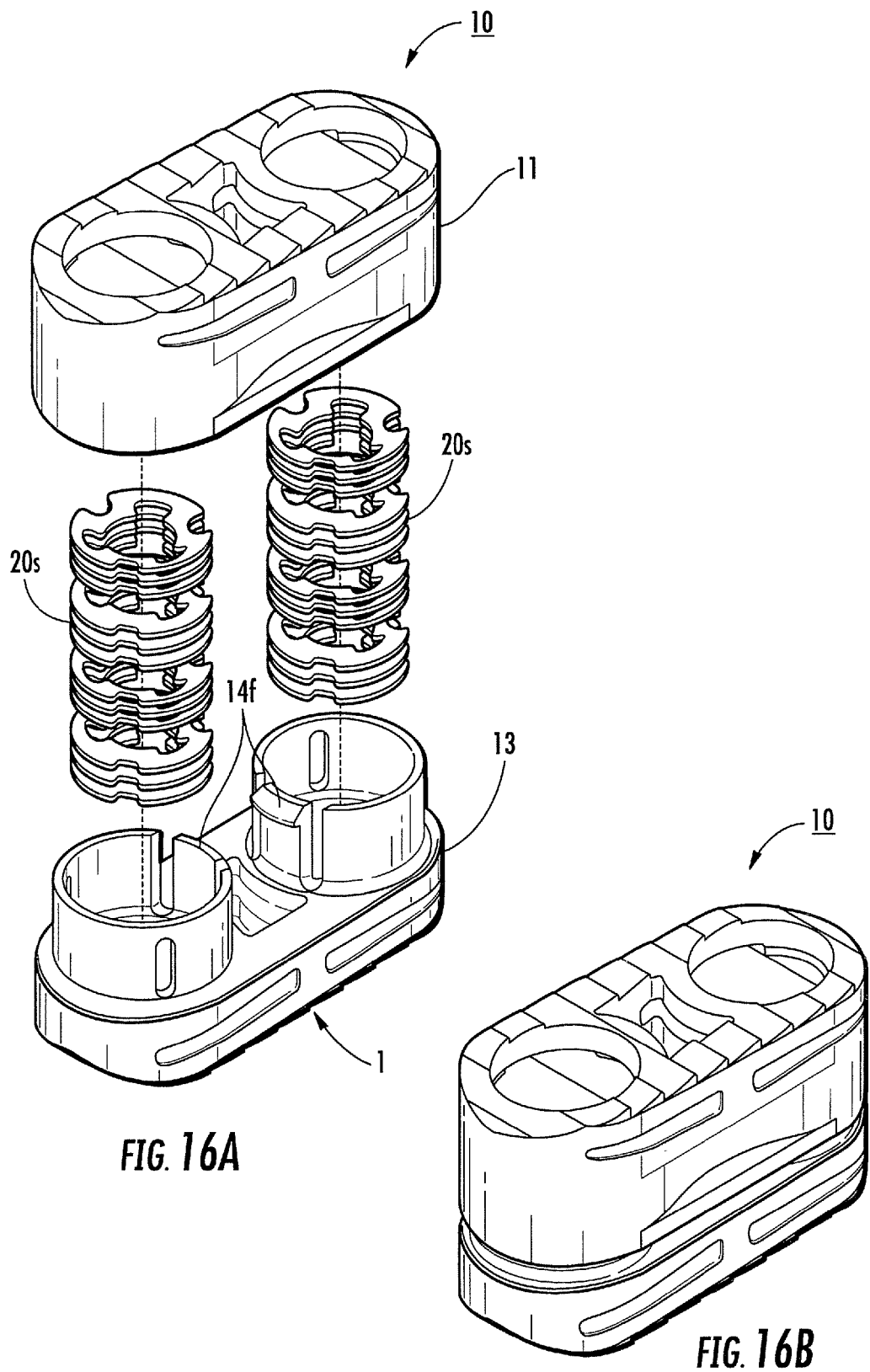
FIG. 16A is an exploded view of an interbody spacer according to embodiments of the present invention.
FIG. 16B is a side perspective assembled view of the device shown in FIG. 16A.
Figure 17A:
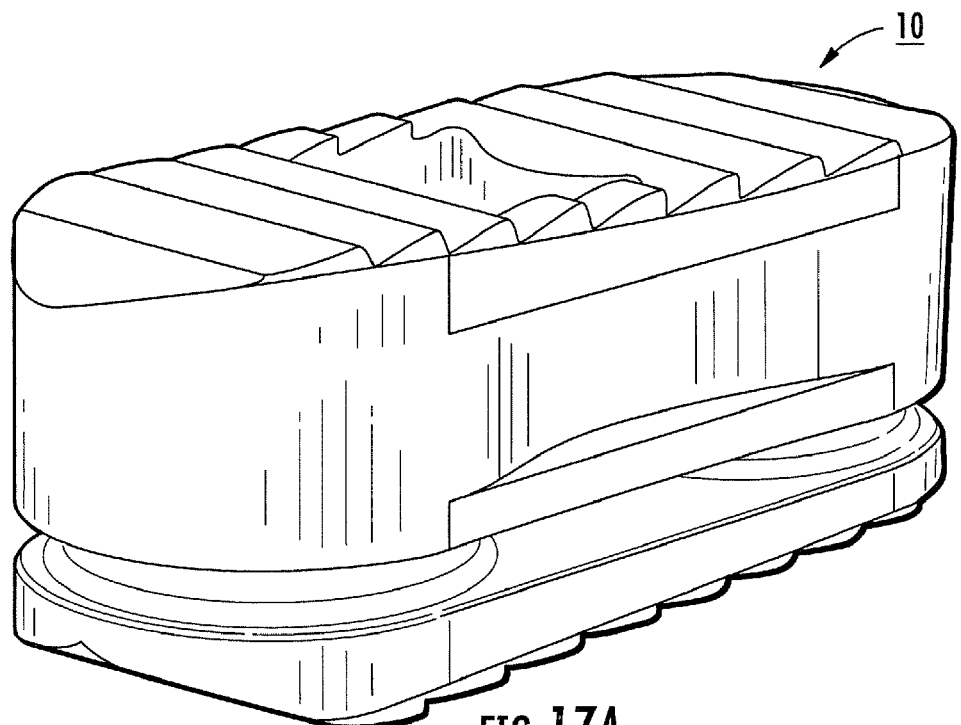
FIG. 17A is a side perspective assembled view of an interbody device according to embodiments of the present invention.
Figure 17B:
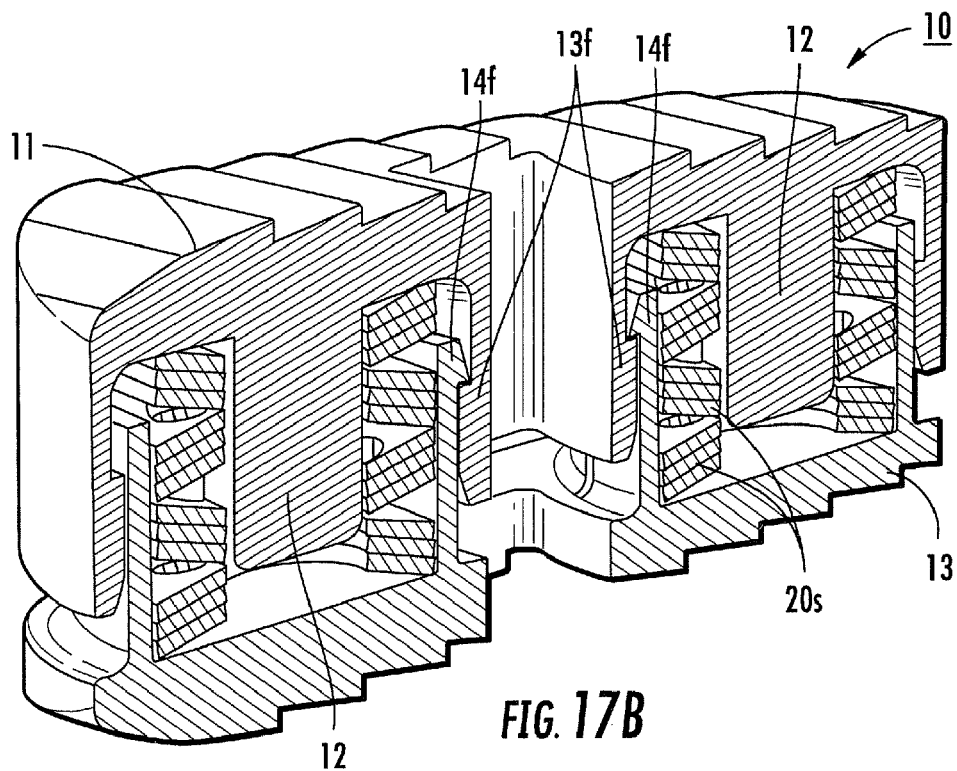
FIG. 17B is a section view of the device shown in FIG. 17A.

FIGS. 16A, 16B, 17A, 17B and 18A all illustrate spacers 10 with elastic members 20 that are defined by or include stacked spring washers 20s such as dome spring disk washers. Suitable dome spring washers are available from Associated Spring Raymond, as Clover Dome spring washers under part no. BC0250-012-S (stainless steel, ¼ inch), with an OD of 6.35 mm and an ID=3.175 mm. In some embodiments, the washers can be stacked in triplet subsets as shown in FIG. 16A and 17B, as sequence "3A3B3A3B" meaning (3 washers in direction A, then 3 oriented in direction B, etc.). In other embodiments, washer pairs can be stacked, AA, BB, AA, BB, AA. Other numbers of washers or washer sub-combinations may also be used. The same or different stack configurations or number of washers in a stack can vary in each chamber in the spacer 10 and the stack can be configured so that the design is a non-repeating pattern. In some embodiments, the spring rate for spacers with two stacks (two chambers, each with a stack) can be between about 300N/mm-800 N/mm (typically about 780 N/mm for a 12 piece stack in the 3A3B3A3B configuration and about 300N/mm for the 10 piece stack configuration discussed above. Although not shown, Belleville washers, wave washers or disc spring washers may also be used alone or in combination with the dome spring washers. However, in some embodiments, the dome spring washers are stacked in series of two or three in different orientations. Also, although shown with a downwardly extending male member, the male member may extend upward or the chambers may contain the washers without any such male member. In some embodiments, the male member(s) can help maintain alignment of the washers in the chamber/cavity when exposed to shear stresses, torsion or other dynamic loads.

FIGS. 19A-C, 20A, 20B, 21A and 21B all illustrate spacers 10 with elastic members 20 that are stacked O-rings. As shown, three O-rings 20o are vertically stacked and abut each other in an annular chamber. However, two, four, five, six or even more O-rings may be used. The male member 12 can extend through a center channel 141 as discussed above and/or include an annular projection that compresses the O-rings. Other attachment configurations can be used.

Figure 18A:
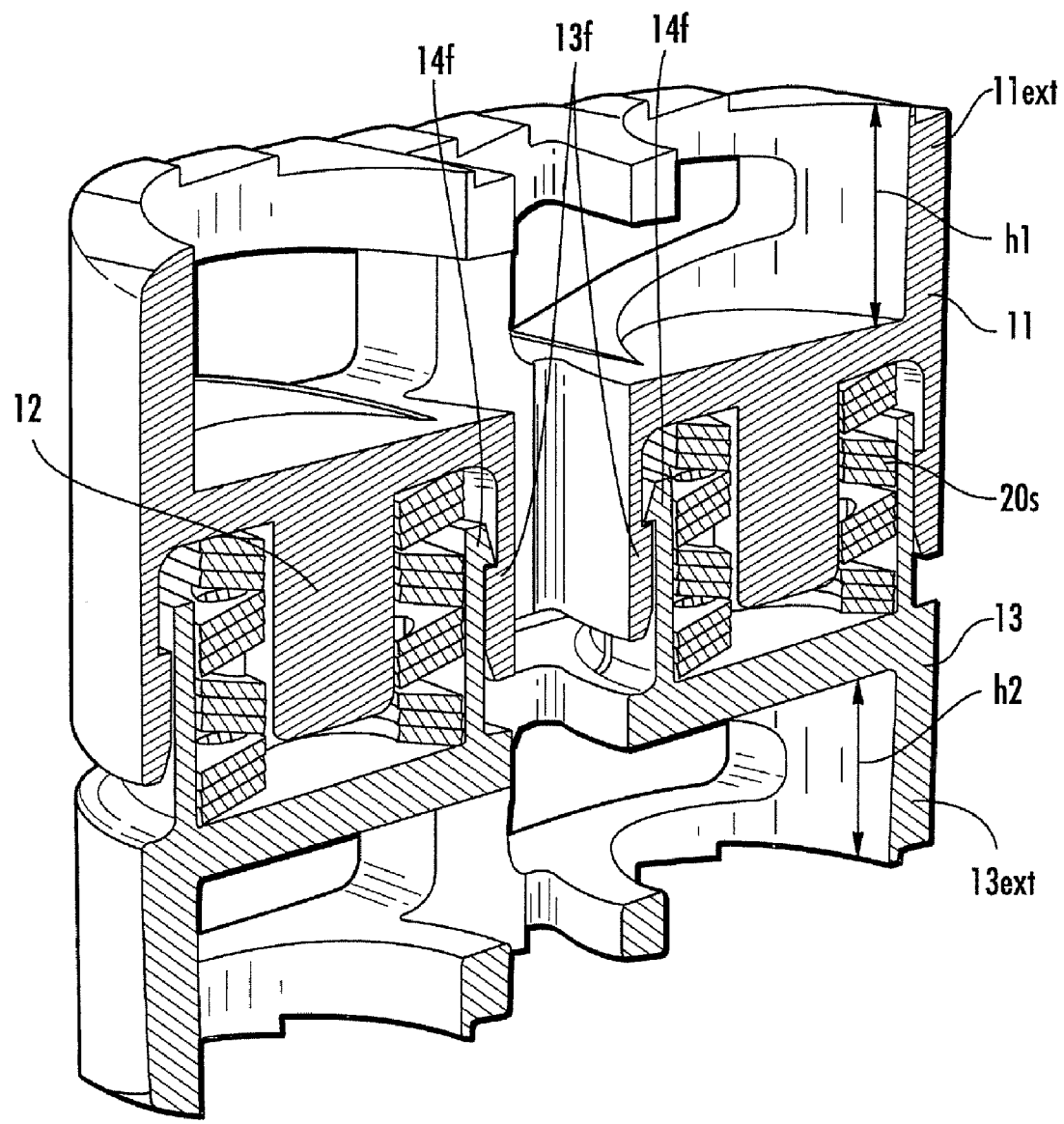
FIG. 18A is a section view of a device similar to that shown in FIG. 16A but with the washers held in towers or extensions according to embodiments of the present invention.
Figure 18B:
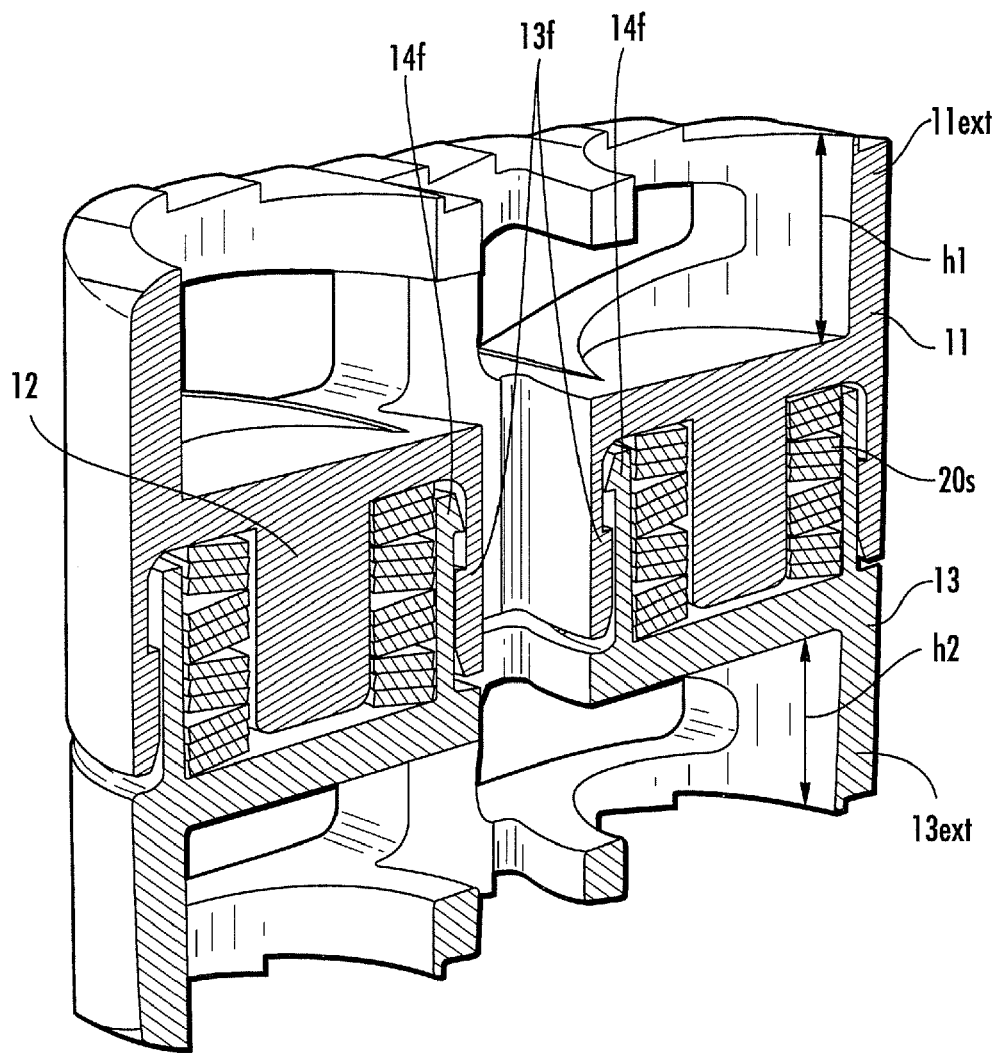
FIG. 18B is a section view of the device shown in FIG. 18A illustrating an exemplary compressed (under load) configuration according to embodiments of the present invention.
Figure 19D:
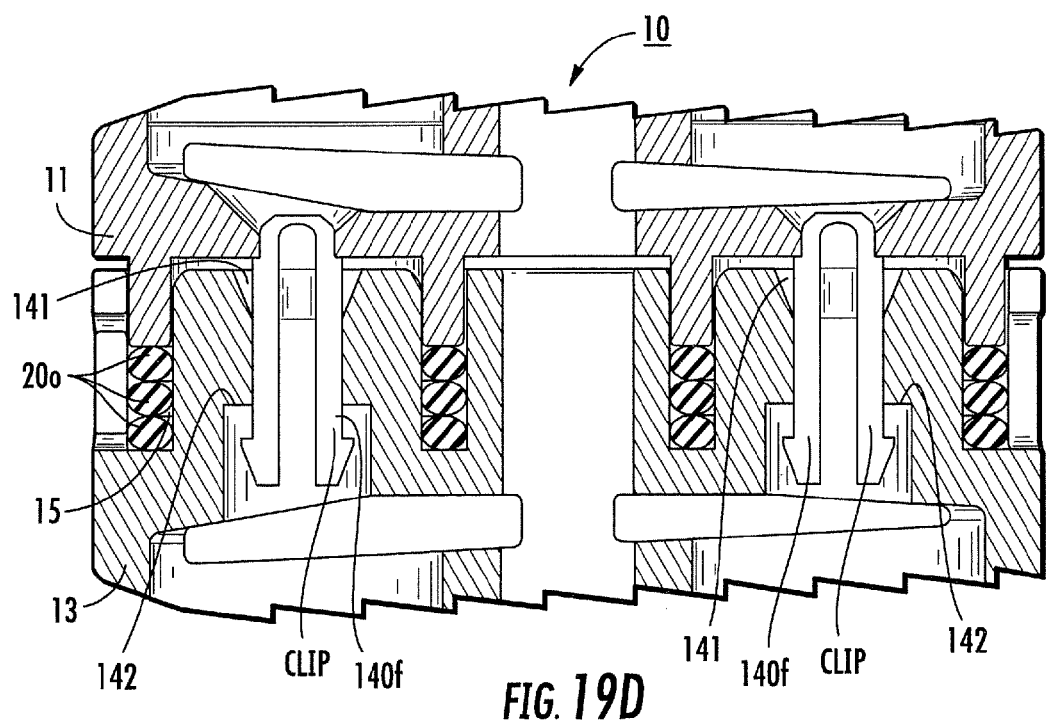
FIG. 19D is a section view of the device shown in FIG. 19C illustrating an exemplary compressed (under load) configuration according to embodiments of the present invention.

FIGS. 18B and 19D illustrate examples of the spacers 10 in an exemplary compressed (loaded) configuration.

The spacers 10 can be evenly distributed structures that are strong, stiff and allow from dynamic stabilization and can withstand normal torsion and shear. The spacers can include openings on the top and bottom for bone in-growth. The devices 10 can include a total lordotic angle of about 5 degrees. In some embodiments, the devices 10 can be configured with dual (or more) independent compressibility upon exposure to forces based on the spaced apart elastic members in two or more chambers. The devices 10 can allow for about 1-2.5 mm of compression, typically about 1 mm compression. The devices 10 can be configured to apply a pre-load onto the resilient member 20 that may be customized to fit the particular implant location and/or patient requirement. The devices 10 can be configured with a "soft stop" that occurs before the maximum "hard stop" of the endplates 11, 13 using the endplate/resilient member 20 configurations described herein which can provide more physiological loading patterns. The elastic member(s) can have variable stiffness, customized stiffness or multiple different stiffnesses.

FIG. 22 illustrates an example of a surgical tool 200 that can be used to place the spacer 10 in the spine. As shown, the tool 200 can include a front lead in chamfer and can include a track on the side for instrument docking. The tool can include a front end 210 that clicks around the implant and a tubular portion can be pushed forward to lock the front end 210. The implant/spacer 10 can be inserted into the spine (and the tool may be suitable for impaction with a mallet on a rear end portion of the hand piece).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A non-articulating semi-rigid spinal implant, comprising:
   upper and lower rigid non-articulating endplates that define at least one aligned pair of substantially rigid male and female members, a respective female member having an interior facing cavity and the respective male member facing toward the female cavity; and
   at least one elastic member in communication with the male member and/or the female member cavity, wherein the at least one elastic member is a resiliently deformable member that changes shape while residing in the female member cavity and defines a soft stop before the endplates with the respective male and female members bottom out during compressive loading, wherein the semi-rigid spinal implant is a spacer for fusion spinal therapy and has dynamic stabilization,
   wherein the lower endplate includes a lower portion with a surface that is configured to contact local bone and a second surface that is vertically spaced apart from and resides above the lower portion, the second surface being attached to the female member, and wherein each respective male member comprises a first end portion that merges into a larger medial portion, with at least one spring held under the larger medial portion about the first end portion, wherein the first end portion of the respective male member is able to travel up and down a distance between about 1-2.5 mm in the respective female interior facing cavity while the at least one spring is held above the respective female cavity under the larger medial portion of the respective male member.

2. A non-articulating semi-rigid spinal implant, comprising:
    upper and lower rigid non-articulating endplates that define at least one aligned pair of substantially rigid male and female members, a respective female member having an interior facing cavity and the respective male member facing toward the female cavity; and
    at least one elastic member in communication with the male member and/or the female member cavity, wherein the at least one elastic member is a resiliently deformable member that changes shape while residing in the female member cavity and defines a soft stop before the endplates with the respective male and female members bottom out during compressive loading,
    wherein the semi-rigid spinal implant is a spacer for fusion spinal therapy and has dynamic stabilization,
    wherein the at least one aligned pair of substantially rigid male and female members is at least two pair, with respective male members comprising a first end portion that merges into a larger medial portion and with at least one spring held under the larger medial portion about the first end portion, wherein the first end portion of the respective male member is able to travel up and down a distance between about 1-2.5 mm in the respective female interior facing cavity while the at least one spring is held above the respective female cavity under the larger medial portion of the respective male member, and wherein the at least one elastic member is a resilient plug that resides inside a respective female cavity.

3. A non-articulating semi-rigid PLIF or TLIF interbody spinal spacer, comprising:
    upper and lower rigid endplates, one having two spaced apart male members and the other having two spaced apart female members, pairs of the male and female members being longitudinally aligned and slidably engaged, each female member having a cavity facing the respective male member; and
    at least one elastic member in communication with the male and female members,
    wherein the at least one elastic member comprises a resiliently deformable member that is configured to define a soft stop before the endplates with the respective male and female members bottom out during compressive loading,
    wherein respective male members comprise a first end portion that merges into a larger medial portion, the spacer further comprising at least one spring held under the larger medial portion about the first end portion, wherein the first end portion of the respective male member is able to travel up and down a distance between about 1-2.5 mm in the respective female interior facing cavity while the at least one spring is held above the respective female cavity under the larger medial portion of the respective male member, and wherein the at least one elastic member is a resilient plug that resides inside a respective female cavity.

* * * * *